(12) United States Patent
Richter et al.

(10) Patent No.: US 11,813,026 B2
(45) Date of Patent: Nov. 14, 2023

(54) SYSTEMS, DEVICES, AND METHODS FOR PROVIDING SURGICAL TRAJECTORY GUIDANCE

(71) Applicant: Medos International Sarl, Le Locle (CH)

(72) Inventors: Joern Richter, Kandern (DE); Marc Puls, Thörigen (CH); Thomas Gamache, Westport, MA (US)

(73) Assignee: Medos International Sarl, Le Locle (CH)

( * ) Notice: Subject to any disclaimer, the term of this patent is extended or adjusted under 35 U.S.C. 154(b) by 1258 days.

(21) Appl. No.: 16/375,987

(22) Filed: Apr. 5, 2019

(65) Prior Publication Data
US 2020/0315711 A1 Oct. 8, 2020

(51) Int. Cl.
| | |
|---|---|
| *A61B 34/20* | (2016.01) |
| *A61B 17/00* | (2006.01) |
| *A61B 34/10* | (2016.01) |
| *A61B 90/00* | (2016.01) |

(52) U.S. Cl.
CPC .............. *A61B 34/20* (2016.02); *A61B 17/00* (2013.01); *A61B 2017/00725* (2013.01); *A61B 2034/107* (2016.02); *A61B 2034/2055* (2016.02); *A61B 2090/3945* (2016.02)

(58) Field of Classification Search
CPC ............ A61B 34/20; A61B 2034/2055; A61B 2090/3945
See application file for complete search history.

(56) References Cited

U.S. PATENT DOCUMENTS

| | | | |
|---|---|---|---|
| 4,573,448 | A | 3/1986 | Kambin |
| 4,646,738 | A | 3/1987 | Trott |
| 4,678,459 | A | 7/1987 | Onik et al. |
| 4,863,430 | A | 9/1989 | Klyce et al. |

(Continued)

FOREIGN PATENT DOCUMENTS

| | | |
|---|---|---|
| CN | 102727309 B | 11/2014 |
| DE | 9415039 U1 | 11/1994 |

(Continued)

OTHER PUBLICATIONS

International Search Report and Written Opinion for Application No. PCT/US2015/043554, dated Nov. 19, 2015 (8 pages).

(Continued)

*Primary Examiner* — Jason M Ip
(74) *Attorney, Agent, or Firm* — Barnes & Thornburg LLP

(57) ABSTRACT

Systems, devices, and methods are provided for trajectory guidance using instrument position data and planned trajectories into or through a patient's body or an object. Lasers are emitted from a laser system toward the patient's body or object at an area within or proximate to the instrument operator's line of sight. Information about the instrument, including the position of its proximal and distal ends, and the position of the patient's body or object, are used to direct the emission of the lasers in real-time during operation of the instrument. The emitted lasers function as visual cues indicating the manner in which to position the distal and proximal ends of the instrument to properly align with the planned trajectory. A guidance map on the instrument can be used to output visual cues about the position of the distal and proximal ends of the instrument relative to a planned trajectory.

16 Claims, 12 Drawing Sheets

(56) References Cited

U.S. PATENT DOCUMENTS

| | | |
|---|---|---|
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey Jr. et al. |
| 5,954,635 A | 9/1999 | Foley et al. |
| 6,033,105 A | 3/2000 | Barker et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,217,509 B1 | 4/2001 | Foley et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,182,731 B2 | 2/2007 | Nguyen et al. |
| 7,341,556 B2 | 3/2008 | Shalman |
| 7,434,325 B2 | 10/2008 | Foley et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Allin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,092,464 B2 | 1/2012 | McKay |
| 8,096,944 B2 | 1/2012 | Harrel |
| 8,202,216 B2 | 6/2012 | Melkent et al. |
| 8,236,006 B2 | 8/2012 | Hamada |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,442,621 B2 | 5/2013 | Gorek et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 2002/0022762 A1 | 2/2002 | Beane et al. |
| 2002/0138020 A1 | 9/2002 | Pflueger |
| 2003/0083555 A1 | 5/2003 | Hunt et al. |

(56) References Cited

U.S. PATENT DOCUMENTS

| | | |
|---|---|---|
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0036264 A1 | 2/2006 | Selover et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0274271 A1 | 11/2009 | Pfister et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0074170 A1 | 3/2014 | Mertens et al. |
| 2014/0107473 A1 | 4/2014 | Dumoulin et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0333208 A1 | 11/2018 | Kotian et al. |

FOREIGN PATENT DOCUMENTS

| | | |
|---|---|---|
| DE | 29916026 U1 | 11/1999 |
| EP | 0 537 116 A1 | 4/1993 |
| EP | 0 807 415 A2 | 11/1997 |
| EP | 3254627 A1 | 12/2017 |
| GB | 2481727 A | 1/2012 |
| NO | 2017/015480 A1 | 1/2017 |
| WO | 96/29014 A1 | 9/1996 |
| WO | 2001/056490 A1 | 8/2001 |
| WO | 2001/089371 A1 | 11/2001 |
| WO | 2002/002016 A1 | 1/2002 |
| WO | 2004/103430 A2 | 12/2004 |
| WO | 2008/121162 A1 | 10/2008 |
| WO | 2009/033207 A1 | 3/2009 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2015142762 A1 | 9/2015 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/083648 A1 | 5/2017 |

OTHER PUBLICATIONS

International Search Report and Written Opinion for Application No. PCT/US2015/048485, dated Feb. 9, 2016. (16 pages).

International Search Report and Written Opinion for Application No. PCT/US2015/060978, dated Feb. 15, 2016 (8 pages).

International Search Report and Written Opinion for Application

(56) References Cited

OTHER PUBLICATIONS

No. PCT/US2016/050022, dated Feb. 1, 2017 (19 pages).

Invitation to Pay Additional Fees for Application No. PCT/US2016/050022, dated Nov. 3, 2016 (2 pages).

Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.

Jung, K., et al., "A hands-free region-of-interest selection interface for solo surgery with a wide-angle endoscope: preclinical proof of concept," Surg Endosc, 2017, v. 31, pp. 974-980.

Invitation to Pay Additional Fees and Partial Search Report for Application No. PCT/IB2020/052932, dated Jun. 9, 2020 (15 pages).

International Search Report and Written Opinion for Application No. PCT/IB2020/052932, dated Jul. 31, 2020 (21 pages).

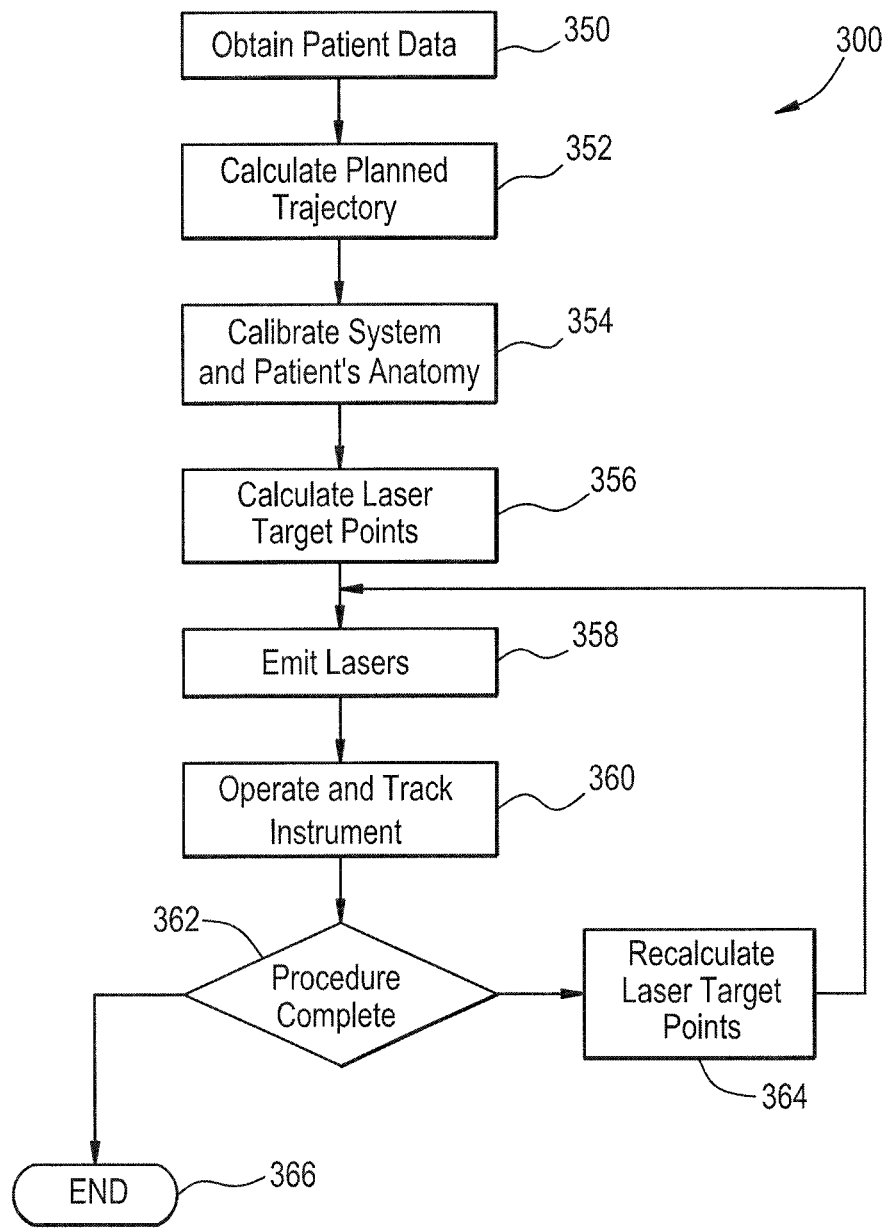

SYSTEMS, DEVICES, AND METHODS FOR PROVIDING SURGICAL TRAJECTORY GUIDANCE

FIELD

The present application relates to trajectory guidance, and more specifically to providing surgical trajectory guidance for surgical instruments.

BACKGROUND

Traditionally, accurate operation of surgical instruments including their movement during surgical procedures is aided by existing navigation systems. These navigation systems use cameras, sensors, and other medical imaging devices such as X-ray and C-arm imaging systems to measure and track the actual and relative position of surgical instruments and of a patient's anatomy during an operation. A number of different tracking modalities can be utilized, including the above-mentioned optical tracking systems, as well as electromagnetic tracking systems (that utilize, e.g., coils and field generators) and others known in the art. A display device of the navigation system that is provided in the surgical room is used to output or display images and other data based on the measured instrument and patient anatomy information, such as the position of the instrument relative to the patient's anatomy.

Such navigation systems are often used to determine whether surgical instruments are being operated in accordance with predetermined or planned trajectories. For example, if a patient is undergoing orthopedic surgery such as spine surgery, a planned trajectory into the patient's body and to the area on the patient's spine where a bone anchor is to be implanted is calculated preoperatively based on three-dimensional images of the patient's surgical area. The planned trajectory refers to a path through which the instrument (and other objects such as a bone anchor) can be advanced and retracted in and out of the patient's body safely or most effectively. During surgery, the position of the instrument and patient's anatomy visualized by the navigation system can be shown, via the display device, relative to the pre-operatively determined trajectory. The surgeon (or other instrument operator) can therefore observe the display device during surgery and operation of the instrument to determine whether the instrument is positioned in alignment with the planned trajectory. To maintain the instrument in its proper alignment or to move the instrument into an aligned position in accordance with the predetermined trajectory, the surgeon in real-time must interpret and/or transform the information shown on the display device into the three-dimensional, real-world surgical area, in order to align the instrument with the planned trajectory. As a result, the surgeon's visual focus and attention on the surgical area and procedure in-progress must be redistributed to repeatedly look at the display device and process the displayed data to monitor and ensure the instrument's alignment with the planned trajectory.

Other systems and devices have been used to guide or ensure instrument alignment in a manner that reduces the impact on the surgeon's attention. These can include the use of surgical robots with navigation systems to mechanically guide the surgeon by placing a guiding tube in alignment with the predetermined trajectory. The surgeon then uses the guiding tube to advance and retract the instrument in and out of the patient's anatomy. These and other existing alternative techniques are bulky, expensive, and/or time-consuming to configure.

Accordingly, there is a need for systems, methods, and devices that guide the positioning of an instrument into alignment with a planned trajectory in a manner that is readily available, intuitive, and minimizes the impact on the surgeon's attention. There is also a need for such systems, methods, and devices to be less expensive than traditional means while providing accurate trajectory guidance for surgical instruments.

SUMMARY

Systems and methods are provided for surgical trajectory guidance. In some example embodiments, a laser system can be used to emit one or more lasers toward the patient's anatomy, indicating how the proximal and distal ends of a surgical instrument should be positioned in order to be aligned with a planned trajectory. The planned trajectory is a path into or through a patient's body, through which the instrument and/or objects are distally and proximally moved. The planned trajectory can be calculated pre-operatively or intra-operatively based on patient data such as medical images of the relevant areas of the patient's anatomy. The patient data and pre- or intra-operatively calculated planned trajectory can be used to calibrate the laser system with the patient in the surgical environment and instruments to be used during the operation. Calibration enables the laser system to translate the calculated planned trajectory into the real-world, three-dimensional space in which the patient is being operated.

With the planned trajectory being applicable to the patient's anatomy in surgery, positions of laser target points on or proximate to the patient's body can be calculated. Emitting lasers onto the laser target points can visually aid a user in positioning an instrument for insertion into, or removal from, a patient's body. In some embodiments, multiple lasers can be emitted (e.g., two lasers in some embodiments). In an embodiment employing multiple lasers, a distal laser can indicate an entry area or entry point on the patient's body where, for example, the distal end of the instrument is to be inserted. A proximal laser can indicate an axis with which the proximal end of the instrument is to intersect when the distal end is aligned with the distal laser to ensure the instrument is aligned with a planned trajectory for its use. In some embodiments, the proximal end of the instrument can include a guide having a target point thereon. The target point indicates where the proximal laser should intersect with the proximal end of the instrument in order to be properly aligned with the planned trajectory. In some embodiments, the laser system can emit a single laser toward a single target point. The emitted laser can be accurately emitted to indicate a longitudinal axis equal to or corresponding to the central longitudinal axis of the planned trajectory. That is, to be in alignment with the planned trajectory, the instrument can be moved such that its distal end and the target point on the guide of the proximal end can be aligned or intersect with the emitted laser. The position of the instrument and/or patient can be tracked in real-time relative to the planned trajectory. The laser target points and direction of emitted lasers can be adjusted in real-time to ensure continued guidance as the instrument is advanced into or retracted from the patient's body.

In other example embodiments, alignment of the instrument with the planned trajectory can be provided using a guide map. The guide map can be a component provided at or proximate to the proximal end of the instrument, and can include embedded LEDs or other light sources that can output visual cues to the operator of the instrument, for example, concerning the position of the instrument. The position of the instrument can be compared with the planned trajectory to determine whether the proximal and distal ends are aligned with a longitudinal axis equal to or corresponding to the planned trajectory. The alignment or misalignment of the distal or proximal ends of the instrument relative to the planned trajectory can cause portions or areas of the guide map to be activated, for example, such that LEDs are illuminated. If the distal or proximal ends of the instrument are misaligned with the planned trajectory, specific LEDs of the guide map can be activated to indicate a direction the distal or proximal ends must be moved to align with the planned trajectory.

In one aspect, a system for providing trajectory guidance is provided that includes one or more laser output devices operable to emit lasers, and at least one processor communicatively coupled to the one or more laser output devices. The at least one processor is operable to calculate a planned trajectory within an object based on first object data corresponding to the object, the planned trajectory indicating a target path for distally and proximally moving one or more instruments in and out of the object. The at least one processor is further operable to obtain actual data including at least second object data corresponding to the object and first instrument data corresponding to an instrument from among the one or more instruments. The at least one processor is further operable to perform calibration on the object and the instrument based on the actual data and the planned trajectory. The at least one processor is further operable to calculate one or more target points based on the actual data and the planned trajectory, each of the one or more target points indicating a position on the object toward which to direct one or more lasers respectively emitted from the one or more laser output devices, and cause to emit the one or more lasers toward the one or more laser target points. Further, the one or more target points are calculated such that the emitted one or more lasers guide the instrument to a planned alignment corresponding to the planned trajectory.

The systems and methods described herein can include any of a variety of additional or alternative features or steps, all of which are considered part of the present disclosure. For example, in some embodiments the planned alignment of the instrument can be a position in which a central longitudinal axis of the instrument is the same as a central longitudinal axis of the planned trajectory. And in some embodiments, the planned alignment can be a position in which a distal portion and a proximal portion of the instrument intersect the one or more lasers.

In certain embodiments, the one or more target points can include a proximal target point and a distal target point indicating a position on the object towards which to direct a proximal laser and a distal laser, respectively. Further, the planned alignment can be a position in which: (1) a distal end of the instrument intersects with the distal laser, and (2) the proximal end of the instrument intersects with the proximal laser. In some embodiments, the proximal end can include a guide having a target point thereon, and the proximal end of the instrument can intersect with the proximal laser at the target point of the guide when the instrument is in the planned alignment. In certain embodiments, the distal end of the instrument can intersect with the distal laser at an entry point into the object, and the entry point can correspond to a proximal end of the planned trajectory. In some embodiments, if the instrument is distally advanced when in the planned alignment, the instrument can move along the planned trajectory.

In certain embodiments, the one or more target points can include a single target point indicating a position on the object toward which to direct a single laser emitted from a single laser output device, the single laser output device being positioned such that a path of the emitted single laser toward the single target point indicates the planned alignment of the instrument. In some embodiments, the path of the emitted single laser can have a central longitudinal axis equal to the central longitudinal axis of the planned trajectory.

In some embodiments, the processor can be further operable to obtain updated actual data including at least updated first instrument data and recalculate the one or more target points based on the updated actual data and the planned trajectory, where the one or more lasers can be caused to be emitted toward the one or more updated laser target points. In certain embodiments, the updated actual data can be based on operating of the instrument. In some embodiments, the obtaining of the updated actual data, recalculating the one or more target points, and causing the one or more lasers to be emitted can be performed in real-time during the operating of the instrument.

In another aspect, a method for providing trajectory guidance is provided that includes calculating a planned trajectory within an object based on first object data corresponding to the object, the planned trajectory indicating a target path for distally and proximally moving one or more instruments in and out of the object. The method further includes obtaining actual data including at least second object data corresponding to the object and first instrument data corresponding to an instrument from among the one or more instruments. The method also includes performing calibration on the object and the instrument based on the actual data and the planned trajectory and calculating one or more target points based on the actual data and the planned trajectory, each of the one or more target points indicating a position on the object toward which to direct one or more lasers respectively emitted from the one or more laser output devices. The method further includes emitting, from the one or more output laser devices, the one or more lasers toward the one or more laser target points. Moreover, the one or more target points are calculated such that the emitted one or more lasers guide the instrument to a planned alignment corresponding to the planned trajectory.

As with the system described above, any of a variety of alternative or additional features can be included. For example, in some embodiments, the planned alignment of the instrument can be a position in which a central longitudinal axis of the instrument is the same as a central longitudinal axis of the planned trajectory. And in some embodiments, the planned alignment can be a position in which a distal portion and a proximal portion of the instrument intersect the one or more lasers.

In certain embodiments, the one or more target points can include a proximal target point and a distal target point indicating a position on the object towards which to direct a proximal laser and a distal laser, respectively, and the planned alignment can be a position in which: (1) a distal end of the instrument intersects with the distal laser, and (2) the proximal end of the instrument intersects with the proximal laser. In some embodiments, the proximal end can include a guide having a target point thereon, and the proximal end of the instrument can intersect with the proximal laser at the target point of the guide when the instrument is in the planned alignment. In some embodiments, the distal end of the instrument can intersect with the distal laser at an entry point into the object, the entry point corresponding to a proximal end of the planned trajectory. In certain embodiments, if the instrument is distally advanced in the planned alignment, the instrument moves along the planned trajectory.

In some embodiments, the one or more target points can include a single target point indicating a position on the object toward which to direct a single laser emitted from a single laser output area, the single laser output area being positioned such that a path of the emitted single laser toward the single target point indicates the planned alignment of the instrument. In certain embodiments, the path of the emitted single laser can have a central longitudinal axis equal to the central longitudinal axis of the planned trajectory.

In certain embodiments, the method can further include obtaining updated actual data including at least updated first instrument data and recalculating the one or more target points based on the updated actual data and the planned trajectory. Moreover, the one or more lasers can be caused to be emitted toward the one or more updated laser target points. In some embodiments, the updated actual data can be based on operating of the instrument. And, in some embodiments, the obtaining of the updated actual data, recalculating the one or more target points, and causing the one or more lasers to be emitted can be performed in real-time during the operating of the instrument.

In another aspect, a system for providing trajectory guidance is provided that includes an instrument including a guide map configured to output visual cues associated with a position of the instrument, the guide map including one or more proximal end areas associated with the a position of a proximal end of the instrument and one or more distal end areas associated with a position of a distal end of the instrument. The system further includes at least one processor communicatively coupled to the instrument, the at least one processor being operable to obtain first guidance data associated with a first position of the instrument at a first time instance, the first guidance data including first distal data corresponding to the distal end of the instrument and first proximal data corresponding to the proximal end of the instrument. The at least one processor being further operable to identify (1) at least one of the proximal end areas of the guide map to activate based on the first distal data and a planned trajectory, and (2) at least one of the distal end areas of the guide map to activate based on the first proximal data and the planned trajectory. The at least one processor being further operable to activate a first portion of the at least one of the proximal end areas of the guide map and a first portion of the at least one of the distal end areas of the guide map identified for activation. Further, the first portion of the at least one of the proximal end areas of the guide map and the first portion of the at least one of the distal end areas that are activated function as visual cues indicating the alignment or misalignment of the proximal and distal ends of the instrument relative to the planned trajectory.

In some embodiments, the one or more proximal end areas of the guide map can include a proximal end alignment area and a proximal end misalignment area, and the one or more distal end areas of the guide map can include a distal end alignment area and a distal end misalignment area. In certain embodiments, the proximal end misalignment area and the distal end misalignment area can be divided into sections. In some embodiments, the first portion of the at least one of the proximal end areas of the guide map and the first portion of the at least one of the distal end areas that are activated can correspond to one or more of the sections of the proximal end misalignment area and the distal end misalignment area, respectively. Moreover, in some embodiments each of the one or more of the sections of the proximal end misalignment area and the distal end misalignment area that correspond to the first portions that are activated can indicate a manner in which to move the proximal end and the distal end of the instrument, respectively, to be aligned with the longitudinal axis of the planned trajectory. And in some embodiments, the first portion of the at least one of the proximal end areas of the guide map and the first portion of the at least one of the distal end areas that are activated can correspond to the proximal end alignment area and the distal end alignment area. Further, in certain embodiments the activation of the proximal end alignment area and the distal end alignment area can indicate alignment of the proximal end and the distal end of the instrument with the longitudinal axis of the planned trajectory.

In certain embodiments, the at least one processor can be further operable to obtain second guidance data associated with a second position of the instrument at a second time instance subsequent to the first time instance, the second guidance data including second distal data corresponding to the distal end of the instrument and second proximal data corresponding to the proximal end of the instrument. The at least one processor can be further operable to identify (1) at least one of the proximal end areas of the guide map to activate based on the second distal data and the planned trajectory, and (2) at least one of the distal end areas of the guide map to activate based on the second proximal data and the planned trajectory, and activate a second portion of the at least one of the proximal end areas of the guide map and a second portion of the at least one of the distal end areas of the guide map identified for activation. Moreover, the proximal end areas of the first portion and the second portion are not identical, and wherein the distal end areas of the first portion and the second portion are not identical, and the first position is different than the second position.

In some embodiments, the system can further include a guidance system communicatively coupled to the instrument and the at least one processor, the guidance system being operable to measure, in real-time, a position of the instrument during its operation, including the first position, and transmit to the instrument the first guidance data including the first position at the first time instance.

In another aspect, a method for providing trajectory guidance is provided that includes obtaining first guidance data associated with a first position of the instrument at a first time instance, the first guidance data including first distal data corresponding to a distal end of the instrument and first proximal data corresponding to a proximal end of the instrument. The method further includes identifying (1) at least one of proximal end areas of a guide map of the instrument to activate based on the first distal data and a planned trajectory, and (2) at least one of distal end areas of the guide map to activate based on the first proximal data and the planned trajectory. The method further includes activating a first portion of the at least one of the proximal end areas of the guide map and a first portion of the at least one of the distal end areas of the guide map identified for activation. Moreover, the first portion of the at least one of the proximal end areas of the guide map and the first portion of the at least one of the distal end areas that are activated function as visual cues indicating the alignment or misalignment of the proximal and distal ends of the instrument relative to the planned trajectory.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which:

FIG. 3 is a flow chart of one embodiment of a process of providing trajectory guidance using the surgical environment of FIG. 2;

DETAILED DESCRIPTION

Figure 1:
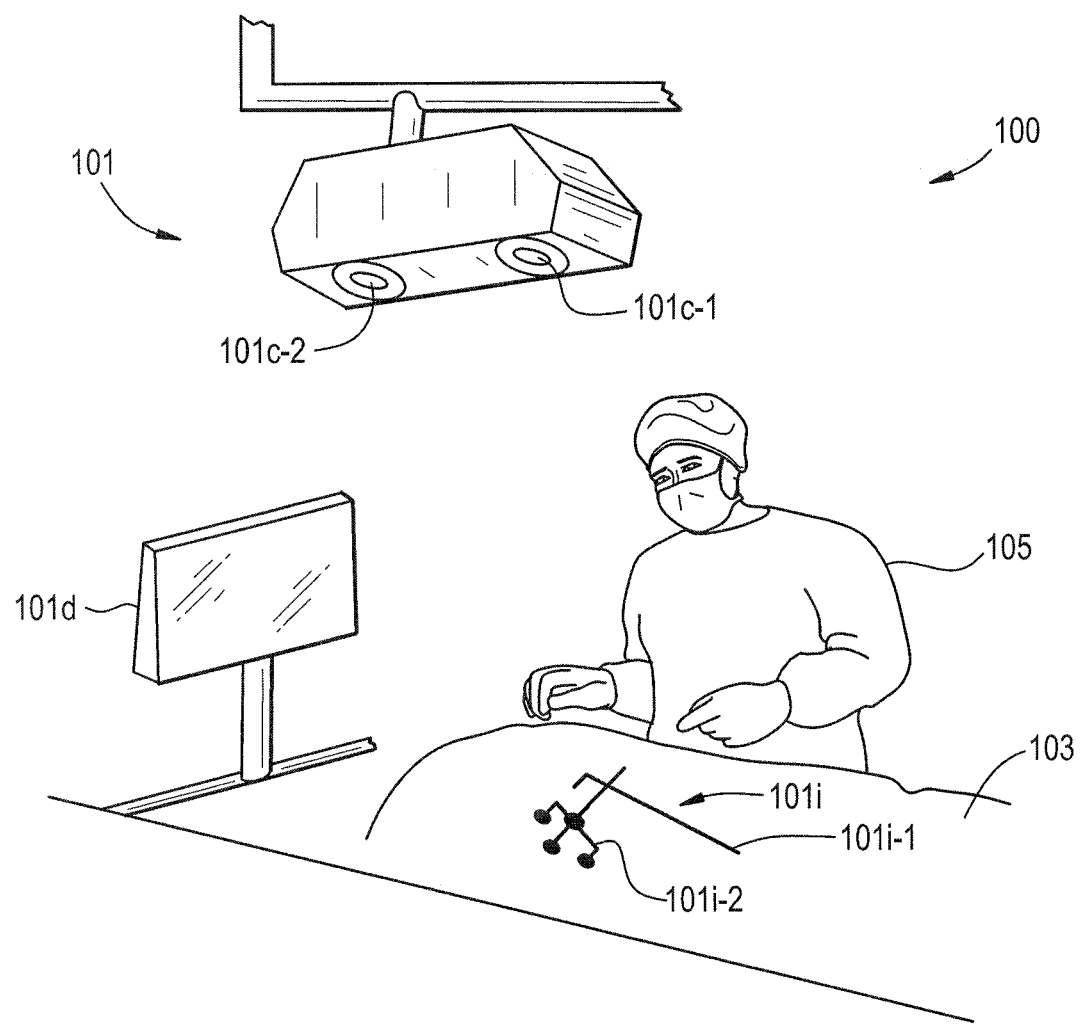
FIG. 1 is a diagram of one embodiment of a surgical environment including a navigation system.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems, devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. Further, to the extent features or steps are described as being, for example, "first" or "second," such numerical ordering is generally arbitrary, and thus such numbering can be interchangeable.

The present disclosure includes some illustrations and descriptions that include prototypes or bench models. A person skilled in the art will recognize how to rely upon the present disclosure to integrate the techniques, systems, devices, and methods provided for into a product, such as a consumer ready, warehouse-ready, or operating room ready surgical system. A person skilled in the art will appreciate that the present disclosure has application in conventional endoscopic, minimally-invasive, open surgical procedures and beyond.

Exemplary embodiments of the present disclosure provide surgical trajectory guidance using lasers. A planned trajectory is a path into or through an object or patient's body, into or via which an instrument or other object is to be inserted and removed. The planned trajectory can be determined pre-operatively or intra-operatively based on patient information including medical imaging, to indicate the safest or most effective path into the patient's body. In surgery, a laser system can be used to emit lasers indicating how an instrument to be inserted into the patient's body should be aligned to conform with the planned trajectory. The lasers are emitted toward target points on or in the direction of the patient's body. The position of the target points is calculated and adjusted accordingly such that the emitted lasers accurately indicate how the distal and proximal ends of the instrument should be aligned. A distal laser emitted toward an entry point on the patient's body indicates or corresponds to where the distal end of the tool should be positioned. The proximal laser indicates a path or axis with which the proximal end of the instrument should be aligned. When the distal end of the instrument aligns with the distal laser and the proximal end aligns with the proximal laser, the instrument is in alignment with the planned trajectory such that, if it is longitudinally moved, its movement will adhere to the planned trajectory. A guide component including a target point thereon can be provided on or proximate to the proximal end of the instrument. The target point of the guide of the instrument indicates the area of the proximal end of the instrument with which the proximal laser should be aligned or intersected.

In some example embodiments, a single laser is emitted toward a single target point on or proximate to the patient's body. The path of the single laser is equal to a longitudinal axis of or corresponding to the planned trajectory. The single laser thus indicates how the distal end of the instrument and the target point on the guide of the proximal end of the instrument should be positioned in order to align with the planned trajectory. When properly aligned, longitudinal movement of the instrument in a proximal and distal direction occurs within or in accordance with the planned trajectory.

In some example embodiments, a guide map can be provided on the instrument, at or near its proximal end. The guide map is a component with portions or areas that can be activated to provide visual cues to the operator of the instrument as to how to position the instrument into alignment with the planned trajectory. The portions or areas of the guide map can be or include LEDs or other light sources indicating alignment and misalignment of the proximal or distal ends of the instrument. If the proximal or distal ends of the instrument are not in alignment with the path or longitudinal axis of the planned trajectory, specific LEDs can be activated or illuminated to indicate how (e.g., the direction in which) the proximal or distal ends should be moved. When the proximal or distal ends are moved in accordance with the activated misalignment LEDs into proper alignment, corresponding alignment LEDs are in turn activated. The instrument can also or alternatively provide haptic and/or audio cues or outputs to indicate position or other relevant information surgical data.

Surgical Navigation

FIG. 1 illustrates a surgical environment 100 including a surgical navigation system 101 for providing guidance and navigation to a surgeon 105 during a surgical procedure of a patient 103. The surgical navigation system 101 is made up of a set of instruments (or tools) and devices that can communicate with one another, and can generate, collect, process, and/or output information for guidance or navigation. Although navigation systems can be made up of a number and variety of instruments and devices, as shown in FIG. 1, the navigation system 101 includes cameras 101c-1 and 101c-2 (collectively "101c"), a display device 101d, and a surgical instrument 101i. The surgical instrument 101i includes a shaft 101i-1 and an instrument array 101i-2. Although not illustrated in FIG. 1, the navigation system 101 can include one or multiple processors and memories, which can be housed together with other instruments and devices of the navigation system 101, or independently. The instruments and/or devices of the navigation system 101 are communicatively coupled via wired and/or wireless communication means such as Wi-Fi, near field communication (NFC), Bluetooth, and other short-range radio frequency means known to those of skill in the art.

Surgical navigation systems, such as navigation system 101, can track the location and position of instruments during a surgical procedure, for example, by identifying the movement of the instrument 101i or instrument array 101i-2 using its cameras 101c. The tracked information concerning the location and position of instruments can be used to calculate and output information, for example, to assist the surgeon 105 (and the like) in adhering to planned surgical steps and processes.

For instance, the navigation system 101 can calculate or receive information regarding one or more target trajectories for the surgeon 105 to execute during a surgery of the patient 103. The target trajectories can refer to a desired or planned path through which a surgical instrument is to be driven, moved or operated, for example, relative to the anatomy of the patient 103. The target trajectories can be calculated in a number of manners either pre-operatively or intra-operatively, including, for example, using three-dimensional (3D) imaging (e.g., CT, MRI) of the patient's anatomy to identify the planned paths therethrough. During the surgery, the navigation system 101 can identify the actual position of the instrument 101i relative to the patient 103. The actual position of the instrument 101i relative to the patient 103 that is identified during the surgery can, in turn, be output on or via the display device 101d, with reference to the previously calculated target trajectories. This allows the surgeon 105 to navigate instruments during surgery by referencing the display 101d of the system 101, and thereby attempt to adhere to the target trajectories.

Although not illustrated in FIG. 1, the navigation system 101 can additionally or alternatively measure or obtain relevant position or location information to provide guidance and navigation by using inertial measurement units (IMUs) and/or other sensors. These IMUs and/or other sensors can be provided or disposed on the instruments, surgical table, patient, and other systems and devices where they, in turn, sensor or collect their position or location information and transmit it to other systems or devices for further processing (e.g., to compare actual instrument operation during surgery to pre-planned target trajectories). Other examples of surgical navigation systems include those that rely on electromagnetic tracking of instruments and other objects in a surgical field using, for example, coils and field generators. Any of a variety of known surgical navigation systems can be utilized in connection with the teachings of the present disclosure.

Laser-Based Trajectory Guidance

Figure 2A:
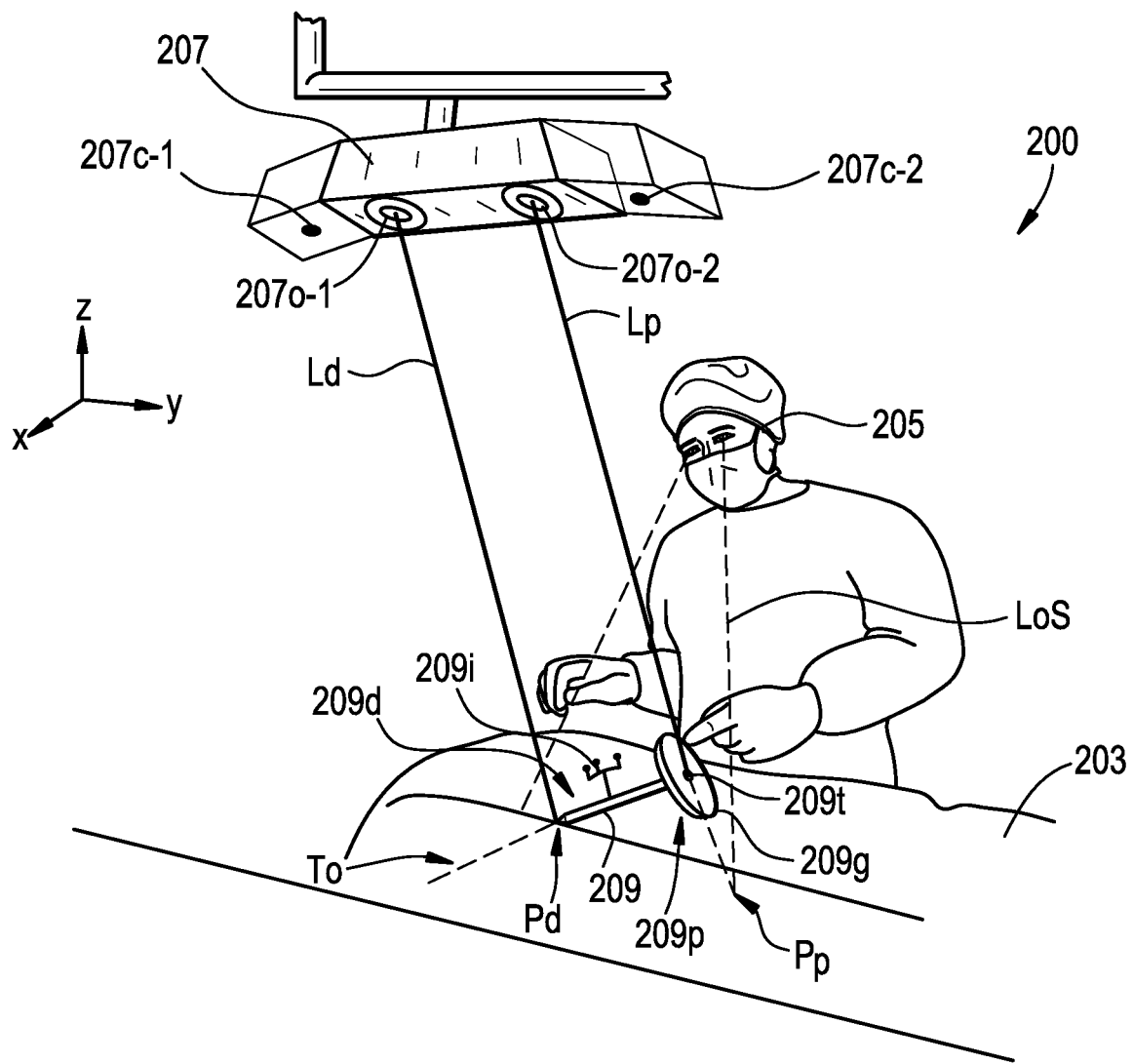
FIG. 2A is a diagram of one embodiment of a surgical environment including a laser system for providing trajectory guidance.
Figure 2B:
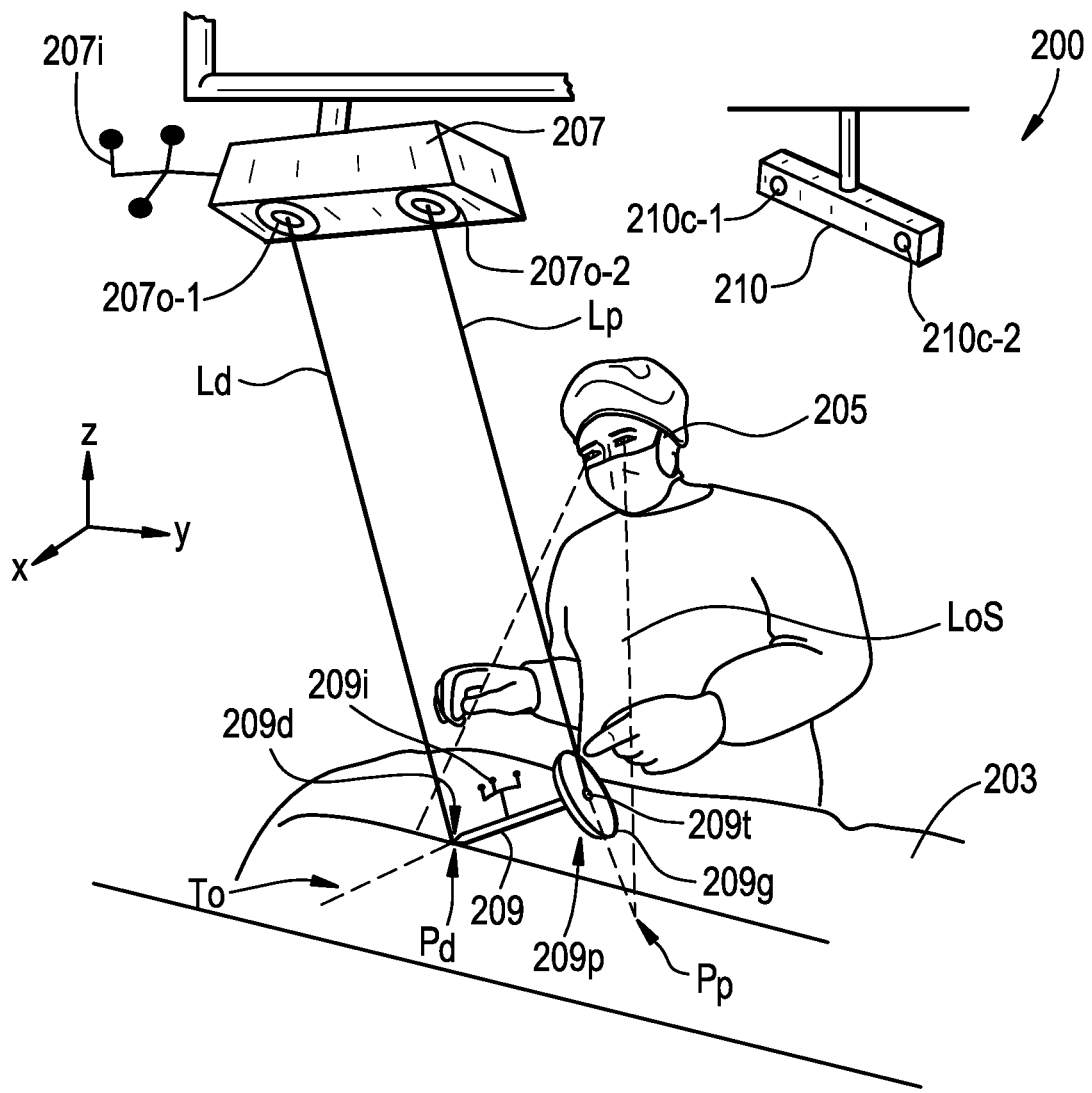
FIG. 2B is a diagram of another embodiment of a surgical environment including a laser system for providing trajectory guidance.

FIGS. 2A and 2B illustrate a surgical environment 200 including exemplary embodiments of a laser system 207 for providing surgical trajectory guidance. The laser systems 207 illustrated in FIGS. 2A and 2B are configured to emit lasers in the direction of the patient 203 to provide trajectory guidance to the surgeon 205. More specifically, the emitted lasers can visually indicate to the surgeon 205 one or more positions that are relevant to achieve planned manipulation of a surgical instrument 209, including its movement along a target trajectory through the body of the patient 203.

Laser systems are devices that are configured to generate and emit light in the form of one or more laser beams. In the exemplary embodiments of FIGS. 2A and 2B, the laser system 207 is configured to generate and emit two laser beams $L_d$ and $L_p$ via respective output or emission devices, components or areas, referred to as laser outputs 207o-1 and 207o-2, though the laser system 207 can be configured to emit any number of laser beams. As explained in further detail below, the laser beams $L_d$ and $L_p$ are emitted such that they provide guidance to or for distal and proximal (or substantially distal and proximal) ends or regions of the instrument 209, respectively. In some embodiments, the laser system 207 can be configured to adjust characteristics of the emitted laser to make them more distinguishable from one another. Non-exhaustive examples of the characteristics that can be adjusted include the color and diameter of the laser beam.

The laser output 207o-1 and 207o-2 can be configured to maximize the directions and areas in or to which the laser beams $L_d$ and $L_p$ can be emitted. For example, the laser outputs 207o-1 and 207o-2 can form part of respective laser emission components that can be driven or adjusted by the laser system 207 as needed. For example, the laser emission components can be designed such that that they can be angled as needed to emit the laser to desired areas on or proximate to the patient 203. Moreover, the laser emission components that include the laser outputs 207o-1 and 207o-2 can be multi jointed (e.g., a multi jointed cylinder) to provide further flexibility. In some embodiments, the laser output components can be mounted or formed on a base of the laser system 207 that can be rotated or moved along the X and Y axes. It should be understood that the design, configuration and/or mounting of the laser outputs 207o-1 and 207o-2 (and/or their laser emission components) can be different for each, such that, for example, one laser output is static relative to the laser system 207, while another is movable and/or adjustable.

Moreover, while the laser system 207 is illustrated in FIGS. 2A and 2B as being part of a single housing, in some embodiments, the laser system 207 is distributed among multiple components and/or housings, which can be communicatively coupled to one another. The laser system 207 can be mounted on a structure (e.g., wall, ceiling), as shown in FIGS. 2A and 2B, or can be provided on a movable system. In some embodiments, the laser system 207 can be fixedly mounted, such that its position is static, or can be mounted on a system of movable arms and/or rails that enable the laser systems 207 (and thus its laser outputs 207o-1 and 207o-2) to be placed in a planned position for emitting lasers $L_d$ and $L_p$, as explained in further detail below.

In order to accurately align the laser outputs 207o-1 and 207o-2 with the positioning of the instrument 209, the laser system 207 can be integrated with a surgical navigation system 101, as described in connection with FIG. 1 above, to accurately determine positions of the laser outputs 207o-1, 207o-2 and the instrument 209. In some embodiments, this can be accomplished using an integrated housing, such as laser system housing 207 shown in FIG. 2A that includes integrated laser outputs 207o-1, 207o-2 along with cameras 207c-1, 207c-2 or other sensors that form the basis of a surgical navigation system. In such an embodiment, the relative positioning of the laser outputs 207o-1, 207o-2 and cameras 207c-1, 207c-2 is fixed. Accordingly, detection of a navigation array 209i coupled to the instrument 209 is sufficient to determine the relative positioning of the instrument and the laser outputs 207o-1, 207o-2.

In another embodiment shown in FIG. 2B, the laser outputs 207o-1, 207o-2 can be integrated into a laser housing 207 that is separate from a housing 210 containing navigation system cameras 210c-1, 210c-2 or other sensors forming the basis of a surgical navigation system 101. In such an embodiment, the laser housing 207 can include its own navigation array 207i (e.g., an array of a plurality of marking spheres), in addition to the navigation array 209i coupled to the instrument 209, such that the navigation system can detect the positions of both the instrument 209 and laser outputs 207o-1, 207o-2 to align them and allow accurate positioning of the laser outputs relative to the instrument.

In any of the above-described embodiments, additional navigation arrays (e.g., navigation spheres for use in optical navigation systems, coils in electromagnetic navigation systems, or other positioning sensors such as inertial motion sensors, etc.) can be utilized in connection with a patient, an operating table, or other objects in the operating environment to allow accurate detection of each object's position and accurate coordination of guidance for a user of a given instrument or object with respect to the patient. Adjustments in alignment between objects and trajectory guidance can be provided in real time intra-operatively to account for deviations from planned trajectories, e.g., due to patient movement, movement of a surgical table due to a bump from a user, etc.

Although not illustrated in FIGS. 2A and 2B, the laser system 207 can include one or more processors, one or more memories, and one or more communication means. The processors can be used, for example, to calculate target trajectories, analyze actual instrument positions, adjust target trajectories, adjust the position of the laser system or its laser outputs, and/or emit and adjust laser beams. The memories can be used, for example, to store software, logic, and/or data relating to the system 207, its outputs 207o-1 and 207o-2, the laser beams $L_d$ and $L_p$, the instrument 209, the patient 203, and or other objects, devices and the like relevant for providing trajectory guidance as described herein. The laser system 207 can include communication means such as antennas and/or radios that enable wired or wireless communications between instruments and/or devices of the system 207, and/or to and from other systems such as cloud computing environments, centralized computing systems, surgical navigation systems, imaging systems, and the like. Non-exhaustive examples of such types of communications protocols and technologies include Bluetooth, Zigbee, Z-Wave, Wi-Fi, cellular, NFC, and others known to those of skill in the art.

Still with reference to FIGS. 2A and 2B, the laser beams $L_d$ and $L_p$ are emitted by the laser system 207 to or toward the patient 203. The laser beams $L_d$ and $L_p$ are configured to visually delineate or mark, for the surgeon's use, relevant points or points of reference for replicating a calculated target trajectory $T_o$. The target trajectory $T_o$, which is illustrated in FIGS. 2A and 2B, is a calculated path through the body of the patient 203, through which the instrument 209 is to be moved to perform a desired surgical function.

The surgical instrument 209 can be or include guidewires, needles, taps, drivers, drills, cutters, blades, bone skids, retractors, access devices, and forceps, as well as implants such as bone anchors, spacers, cages, rods, plates, connectors, and the like. The instrument 209 includes a distal end 209d, initially positioned closest to the patient 203, and a proximal end 209p, initially positioned away from the patient 203. As noted above, the instrument can include a navigation array or sensor 209i to allow its position to be tracked by a navigation system integrated with the laser system. As explained in further detail below with reference to FIG. 3, in some embodiments, providing trajectory guidance for the instrument 209 by (1) directing the emitted laser $L_d$ toward a surgical area, and particularly to a point of entry where the distal end 209d of the instrument 209 should (e.g., to replicate the target trajectory To) be inserted; and (2) directing the emitted laser $L_p$ toward the surgical area of the patient 203, to indicate the planned position at which a guide 209g and a target 209t on the guide 209t should be positioned to replicate the target trajectory $T_o$. Notably, the lasers $L_p$ and $L_d$ are therefore emitted in the direction of the surgical area of the patient 203, which substantially corresponds with the line of sight (LoS) of the surgeon 205 during the surgical procedure.

More specifically, the instrument 209 can include a guide 209g on or proximate to its proximal end 209p. In some embodiments, the guide 209g is a circular plate, though the guide 209g can be of different shapes and have different characteristics. Moreover, in some embodiments, the guide 209g includes a target point 209t corresponding to the center of the guide 209g and thus the planned point with which the laser beam $L_p$ is to be aligned or is to intersect, in order to replicate the planned trajectory $T_o$. The target point 209t can marked by a shape such as a circle or X on the center of the guide 209g, for example, using a different color than other adjacent portions of the guide 209g. In some embodiments, the guide 209g is modular, such that it can be added and removed from the instrument 209 and thus interchangeable between instruments. The guide 209g can also be configured to be movable when disposed on the instrument 209. For instance, the guide 209g can be pivotable relative to the shaft of the instrument 209 to optimize the ability to align the guide 209g and/or its target point 209t to the laser beam $L_p$.

Operation of the laser system for providing laser-based trajectory guidance is now described with reference to FIGS. 3 to 5B.

FIG. 3 is a flowchart 300 illustrating one exemplary embodiment of a process for providing laser-based trajectory guidance using the laser system 207. More specifically, in the flowchart 300, the laser system 207 outputs laser beams $L_d$ and $L_p$ toward a patient 203, to guide the movement of an instrument 209 along a planned trajectory $T_o$ by the surgeon 205.

At step 350, patient data of the patient 203 is obtained by the laser system 207. The patient data can include anatomical data and/or images of the patient 203 (e.g., CT, MRI, X-Ray) as well as other information that is relevant to the surgical procedure of the patient (e.g., age, weight, height, procedure, etc.). The patient data obtained at step 350 can be generated pre-operatively or intra-operatively. As described in further detail below, the patient data obtained at step 350 includes at least sufficient information to calculate the planned or target trajectory $T_o$ for the instrument 209.

In some embodiments, the patient data can be received from one or more systems or devices that are communicatively coupled to the laser system 207. For example, images of the relevant areas of the patient's anatomy (e.g., the surgical site) can be received directly from an imaging system or an imaging database that stores patient scans. Patient data can be received by the laser system 207, for example, from a healthcare provider system that stores information related to patients (e.g., patient 203), such as patient symptoms, diagnosis, planned procedure, and the like, as known to those of skill in the art. In some embodiments, part or all of the patient data can be obtained from one or more devices or components that are part of the laser system 207. For instance, patient data can be stored on one or more memories of or associated with the laser system 207 and retrieved therefrom at step 350.

In turn, at step 352, a target or planned trajectory $T_o$ is calculated. As described herein, the planned trajectory $T_o$ refers to a path into and/or through the patient's anatomy, which indicates the planned angle, direction and/or depth to which the instrument 209 should be advanced and/or retracted. The target or planned trajectory can be calculated by the laser system 207 based on the patient data obtained at step 350. For example, patient data such as the patient images, diagnosis, and planned procedure can be analyzed to determine the required instruments and their planned manipulation during the surgery, including the trajectory to and through which they should be moved. Alternatively or additionally, in some embodiments, the planned trajectory $T_o$ can be calculated at step 352 based on information input by medical professionals, such as the surgical opinion and plan of the surgeon 205, and/or on expert medical data (e.g., research, manuals, journals, etc.).

For example, in the context of a spinal surgery, the instrument 209 can be a bone anchor driver loaded with a bone anchor to be inserted or implanted into a pedicle of the patient 203. Accordingly, the laser system 207 can obtain images such as an MIl of the spine of the patient 203 at step 350 and, in turn, calculate the planned trajectory $T_o$ of the driver 209 into the patient's body and pedicle, at step 352, based on the obtained images and, for example, information input by or from the surgeon 205.

It should be understood that the calculated trajectory $T_o$ can be in the form of an image (e.g., a path illustrated on an image of the relevant portion of the body of the patient 203) and/or information defining the planned trajectory $T_o$. The information defining the planned trajectory $T_o$ can include angles, depths, entry points, and the other information that is relevant to the operation of the instrument. This information can be measured and/or provided relative to points of reference including markers and/or anatomical landmarks of the of the patient 203, such as a pedicle or pedicle center, spinous process edge, midline axis, or intervertebral disc. By defining the planned trajectory information $T_o$ relative to points of reference, the planned trajectory $T_o$ can be translated from a theoretic calculation by the system 207 into a real-world surgical environment where it can be applied or replicated on the patient 203. The relevant markers and/or landmarks that are used in some embodiments to define the planned trajectory $T_o$ can be accounted for or included in the patient data obtained at step 350. That is, for example, the markers and/or landmarks can be included, highlighted or otherwise illustrated in images of the patient's anatomy. In other embodiments, the laser system 207 can be integrated with a surgical navigation system 101, as described above in connection with FIGS. 2A and 2B. In such embodiments, planned trajectory information $T_o$ can be accurately displayed with relation to a patient's position in the operating environment based on detection of positions of the patient, laser system 207, instrument 209, and/or other objects by the surgical navigation system. Further, continuous detection of object positions by the surgical navigation system can allow the planned trajectory information $T_o$ and other relevant surgical information displayed or otherwise conveyed to a user to be continuously updated intra-operatively to account for changes in object positioning relative to originally created planned trajectory information $T_o$ or other relevant surgical information. This can allow the combination of the surgical navigation system and laser system to adapt a plan created pre-operatively or intra-operatively in real-time in response to, for example, patient movement or other object movement in the operating environment (e.g., table bumps or other intended or unintended object movement, etc.).

Further, note that the planned trajectory information $T_o$ can be determined intra-operatively in a variety of manners. In some embodiments, for example, medical imaging or other data gathering techniques can be utilized intra-operatively in a manner analogous to how they can be used pre-operatively. In some embodiments, however, the planned trajectory information $T_o$ can be determined based on a user positioning an instrument in a desired orientation and using sensors, such as those comprising a surgical navigation system, to detect the positioning and orientation of the instrument and using it to set planned trajectory information $T_o$. For example, a user can hold an instrument, such as a pointer device, at a desired entry point and aligned with a desired trajectory and its position can be captured by a surgical navigation system or any of a variety of sensors of various modalities (e.g., optical, electromagnetic, etc.). In such a case, any emitted lasers can be moved to match the positioning of the instrument and at the time the planned trajectory information $T_o$ is set and can subsequently guide the instrument as it is utilized during a procedure.

Returning to FIG. 3, at step 354 the laser system 207 and patient's anatomy are calibrated, for example, during, preceding, or immediately preceding the surgical procedure of the patient 203. The calibration of step 354 can be performed to correlate (1) the patient's anatomy as defined by or in the patient data and/or the calculated planned trajectory $T_o$, and (2) the patient's real-world anatomy at the time of the surgery. The calibration of step 354 enables the translation of the planned trajectory $T_o$, which is calculated based on patient imaging and other data, into a real-world trajectory that can be replicated on the patient 203. The calibration can be performed using various tools and techniques known to those of skill in the art, including comparing artificial markers and/or other anatomical landmarks from the pre-operative patient data and/or imaging of the patient 203 to or with respective markers and/or anatomical landmarks of the patient 203 in the surgical environment. For example, as known to those of skill in the art, the distance between two markers in a pre-operative image of the patient 203 can be compared with the distance between the same two markers at or preceding the surgery (or two corresponding markers positioned similarly to the respective markers in the pre-operative image). Such a comparison can provide a ratio between the pre-operative data or image and the actual in-surgery patient 203. This ratio, and other data gathered from the correlation can be used to calibrate the laser system 207, enabling the laser system 207 to execute real-world actions (e.g., manipulations, adjustments) that match or adhere to the pre-operatively calculated target or planned trajectory $T_o$. Moreover, in embodiments utilizing or including a surgical navigation system to track portions of patient anatomy, instruments, implants, laser system components, or other objects in real time, the calibration of step 354 can be performed continuously and in real time throughout an operation, and may result in one or more of the above-noted calibration methods being unnecessary in view of the surgical navigation system tracking objects and/or patient anatomy in the operating environment.

The in-surgery information with which the pre-operative or intra-operative data (e.g., patient data, patient images) is correlated for the calibration of step 354 can be obtained in various ways, including use of the surgical navigation systems described above. By way of further example, in some embodiments IMUs and other sensors configured to measure specific force, angular rate, magnetic field, rotation (e.g., pitch, yaw, roll), acceleration, position, location, and angular reference, among other data, can be placed at relevant areas in the surgical environment, such as on the patient's body, surgical table, surgical instruments, and/or other systems and devices (e.g., laser system, navigation system, imaging device, etc.). Position sensors can measure absolute and/or relative positions along multiple (e.g., two, three) axes. The position information sensed or obtained by the sensors (e.g., in the operative environment) can be transmitted to communicatively coupled systems and devices including, for example, other sensors and/or the laser system 207. In some embodiments utilizing pre-operatively generated data, for example, to correlate the anatomy of the patient 203 in-surgery with the patient data (e.g., patient imaging) obtained pre-operatively at step 350 that is used to calculate the planned trajectory $T_o$, the sensors can be placed at areas corresponding to markers or anatomical landmarks identified or identifiable in the patient data. In this way, in-surgery data about the patient 203, such as the actual or real-world distance from one anatomical landmark to another, can be detected or calculated and, in turn, compared or correlated with the pre-operative patient data obtained at step 350. In other words, the calibration of step 354 enables the system 207 to translate a coordinate (e.g., instrument insertion point) on an image of the patient's body obtained from a pre-operative patient image into a real-world coordinate on the patient's body in surgery.

The calibration of step 354 can also or alternatively include calibration of the laser system 207 and other instruments, systems, and/or devices. For example, at step 354, the instrument 209 can be calibrated to the laser system 207 and/or to the patient 203 using sensors placed thereon, as discussed above. Similar to the calibration of the in-surgery patient anatomy describe above, sensors included or placed on instruments, systems and/or devices such as the instrument 209 can be used to detect or measure their actual and/or relative positions, and transmit the sensed information to other communicatively coupled sensors (e.g., sensor-equipped instruments), systems and/or devices. This enables the laser system 207 to identify or calculate how the instrument 209 is manipulated during surgery, including, for example, how the instrument 209 is being moved and/or operated relative to the patient's body and the patient's surgical area. In some embodiments, the calibration of the laser system 207 and/or other instruments, systems and devices enables the laser system 207 to determine whether the instrument 209 is being moved in accordance with the planned trajectory calculated at step 352, and to make or trigger adjustments as needed, as described above.

As also noted above, in addition or alternative to calibrating using IMUs and other sensors that sense and transmit information such as position data, calibration can be performed using surgical navigation software and hardware, which can include one or more cameras (or imaging devices) and reference arrays that are configured to be identified by the cameras. Reference arrays can be provided on or attached to objects, systems, devices, and patients, including, for example, the instrument 209 (as shown in FIGS. 2A and 2B) and/or the patient 203. The cameras can therefore calibrate the laser system 207 and/or the patient 203 by measuring relevant information (e.g., distances, positions, angles, etc.) using strategically positioned cameras and reference arrays to obtain real-world data that can be correlated with the pre-operatively obtained patient data and/or the calculated planned trajectory $T_o$.

Surgical navigation can in some cases be provided using navigation hardware and software included in an independent navigation system, as shown in the embodiment of FIG. 2B, while in other embodiments such hardware and software can be integrated into the laser system, as shown in FIG. 2A. Accordingly, in some embodiments in which the laser system 207 employs robotic navigation techniques, such as the calibration of step 354 (and/or the tracking of the surgical instrument of step 360 described below), the laser system 207 can include such navigation hardware and/or software. For instance, the laser system 207 can include cameras configured to, for example, image a surgical environment, including the patient, surgeon, instruments, and the like. On the other hand, in some embodiments, the laser system 207 does not include the navigation hardware and/or software and, rather, the laser system 207 is communicatively coupled to a separate navigation system that provides surgical navigation.

Still with reference to FIG. 3, in some embodiments, the calibration performed at step 354 can consider or be based in part on known or previously acquired information about systems, devices, instruments, and/or anatomical parts of the patient. For example, a system can require knowledge of dimensions of an instrument (e.g., its length) in order to accurately project laser visual indicators to direct use of the instrument. This known information can be stored on the laser system 207 or obtained from a third party storage system or the like. For example, when calibrating the system 207 to the instrument 209, the system 207 can retrieve and/or use the dimensions of the specific type of instrument 209. Because the dimensions of the instrument 209 can, in some embodiments, be constant based on the type of instrument, the laser system 207 can calibrate without needing to measure the instrument 209. As described in further detail below, for example, with reference to step 360, calibrating the system 207 to other instruments, systems, and/or devices such as the instrument 209, enables the system 207 to track the position, movement, and other features of the instrument 209 during surgery (and/or portions thereof, such as the instrument guide 209g or its target point 209t), both relative to itself, the patient, and to other instruments, systems and devices.

Figure 4A:
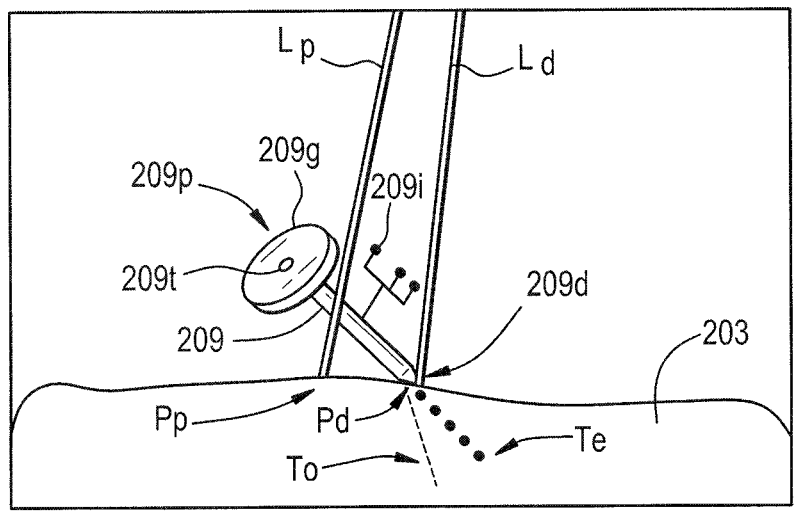
FIG. 4A is diagram of one embodiment of multiple emitted lasers providing trajectory guidance for a surgical instrument at a first time period.
Figure 4B:
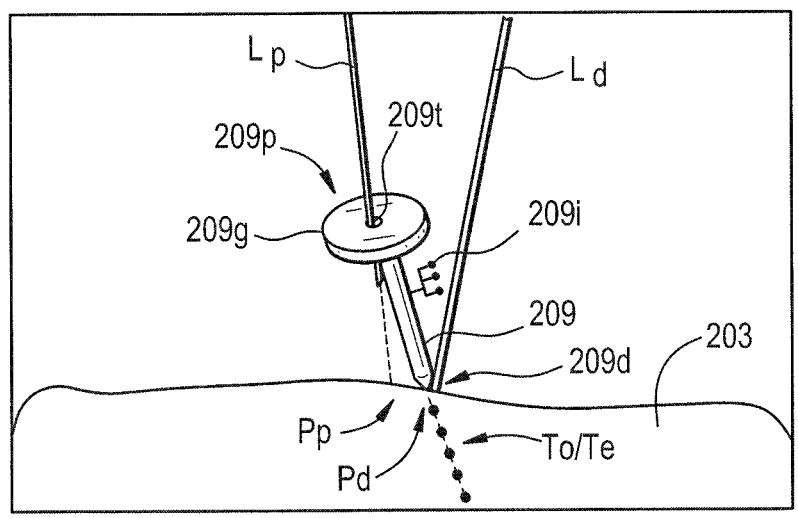
FIG. 4B is a diagram of one embodiment of multiple emitted lasers providing trajectory guidance for the surgical instrument of FIG. 4A at a second time period.
Figure 4C:
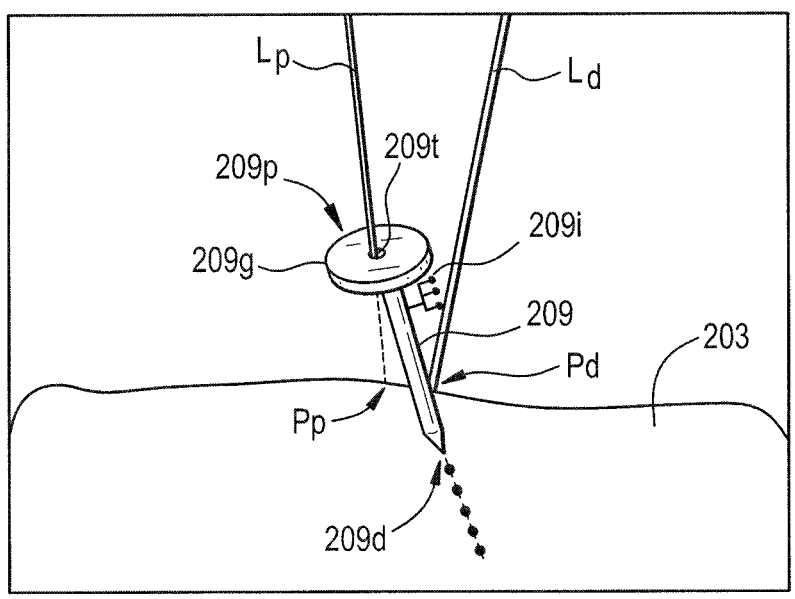
FIG. 4C is a diagram of one embodiment of multiple emitted lasers providing trajectory guidance for the surgical instrument of FIGS. 4A and 4B at a third time period.

At step 356 the laser system 207 calculates one or more target points. The target points are points where or in the direction in which the lasers emitted by the laser system 207 are to be aimed or directed. As described above, in some embodiments, trajectory guidance is provided by emitting two lasers $L_d$ and $L_p$ from the laser system 207 in the direction of the patient, to indicate or guide (1) where the distal end 209d of the instrument 209 is to be inserted into the patient 203, and (2) how the proximal end 209p of the instrument 209 is to be aligned to replicate the planned trajectory $T_o$ calculated at step 352. Accordingly, in such embodiments, the laser system 207 calculates the position of two target points, a proximal end target point $P_p$ and a distal end target point $P_d$, located on or proximate to the patient 203 where the lasers $L_d$ and $L_p$ are to be emitted. It should be understood that the point $P_p$ on or near the patient's body corresponds to the area toward which the laser $L_p$ is to be emitted. However, because the objective of the trajectory guidance described herein is in some embodiments to align the guide 209g of the instrument 209 with the laser $L_p$, the laser $L_p$ can in some cases not be visible at or near the point $P_p$, despite being emitted in its direction, due to the guide 209g being aligned in a manner that interferes with the path of the light of the laser $L_p$. FIGS. 4A to 4C, described in further detail below with reference to steps 358 and 360, illustrate exemplary embodiments of the emission of lasers $L_d$ and $L_p$ toward calculated respective points $P_d$ and $P_p$.

The target points $P_p$ and $P_d$ can be calculated based on (1) data defining the planned trajectory $T_o$ calculated at step 352, and/or (2) data obtained or obtainable by the laser system 207. As described above, the planned trajectory $T_o$ calculated at step 352 is a path in the body of the patient 203, through which the instrument 209 is advanced (and/or retracted) to perform a surgical step or process. The planned trajectory $T_o$ can be defined by angles, depths, entry points, and the like. As also described above, the data obtained or obtainable by the laser system 207 can include information about the patient 203, instrument 209, laser system 207, and other systems, devices, and instruments. Such information can include actual or relative positions, angles, and the like. The pre-operative measurements and data defining the planned trajectory $T_o$ can be converted into real-world data applicable to the in-surgery patient 203.

In some embodiments, the target distal point $P_d$ can be calculated, for instance, by determining the point on the patient's body at which the instrument 209 should be inserted to adhere to the planned trajectory $T_o$. The target proximal point $P_p$ indicates where the laser $L_p$ should be directed in order to create a laser beam that, when intersected by the instrument 209 at the target point 209t of its guide 209g, indicates the proper alignment of the proximal end in order to replicate the planned trajectory $T_o$. Thus, the target proximal point $P_p$ can be calculated, for example, based on information about the objective trajectory $T_o$ (e.g., angle), the length of the instrument 209, the position 203 and the instrument 209 (e.g., relative to one another or to the laser system 207), and other data as known to those of skill in the art.

In turn, at step 358, the laser system 207 emits lasers (e.g., lasers $L_p$ and $L_d$) corresponding and directed to the target points (e.g., points $P_p$ and $P_d$) calculated at step 356. As described above, in some embodiments, the emitted lasers can have different characteristics to make them distinguishable from one another. For example, the lasers can be of different colors or have beams of different diameters.

As shown in exemplary FIGS. 2A and 2B, the lasers can be emitted from respective laser output areas that can be moved, pivoted, rotated, and/or otherwise adjusted as needed to emit the lasers to or toward the target points. Accordingly, at step 358, the laser system 207 determines its position relative to the patient 203 and/or the position of its output areas, and makes adjustments as needed. As described above, the laser system 207 can be movably positioned (e.g., on a rail system) such that it can be driven to any desired location. In turn, the laser $L_p$ and $L_d$ are emitted from the positioned laser system 207 and/or output areas, thereby providing guidance to achieve the planned trajectory $T_o$.

It should be understood that, in some embodiments in which the laser system 207 is communicatively coupled to a surgical navigation system and physically movable relative thereto (e.g., as shown in FIG. 2B), the navigation system can calculate the planned position of the laser system 207 and/or its output areas to emit the lasers to or toward the target points $P_d$ and $P_p$. The position information can be transmitted to the laser system 207 to enable it to cause its movement accordingly, or the navigation system can instruct and/or trigger the laser system 207 to be driven to the planned positon.

Once the lasers have been emitted at step 358, the surgical instrument 209 can be placed and/or manipulated to engage in the desired surgical step or procedure. That is, at step 360, the instrument 209 is operated by a surgeon, medical professional or the like, for example, by placing the distal end of the instrument 209 at the surgical entry point on the patient 203. The instrument 209 can be manipulated and adjusted as needed to achieve a desired alignment corresponding to the planned trajectory $T_o$. Moreover, as described in further detail below, the operation of the instrument 209 can be tracked in real-time by the laser system 207 (and/or interconnected surgical navigation system), to make adjustments as needed in order to achieve desired instrument guidance. The operation of the surgical instrument 209 performed at step 360 (as well as the laser emission of step 358) is described with reference to FIGS. 4A-4C.

FIGS. 4A, 4B, and 4C illustrate exemplary embodiments of the emission of lasers $L_p$ and $L_d$ to provide trajectory guidance for the instrument 209 during three sequential time periods to t2, respectively. As shown, lasers $L_p$ and $L_d$ are emitted (e.g., as in step 358) to or toward the target points $P_p$ and $P_d$, respectively, on the body of the patient 203 to guide the trajectory of the surgical instrument 209 during a surgical step or procedure. More specifically, the lasers $L_p$ and $L_d$ are emitted such that when (1) the distal end 209d of the instrument 209 is aligned with the target distal point $P_d$, and (2) the target point 209t on the guide 209g of the instrument 209 (at or near its proximal end 209p) is aligned with (e.g., intersects with) the laser $L_p$ directed toward the target proximal point $P_p$, the instrument 209 is considered to be properly aligned in order replicate the planned trajectory $T_o$. In some embodiments, proper alignment of the instrument 209 to replicate the planned trajectory means that the instrument 209 (e.g., at an elongate shaft portion or the like) has the same (or substantially the same) central longitudinal axis as the planned trajectory $T_o$, or that an angle formed between the elongate shaft of the instrument 209 and the planned trajectory $T_o$ is equal to (or substantially equal) 180 degrees.

As shown in FIG. 4A, at a first time period t0, the instrument 209 is positioned such that its distal end 209d is in contact and/or adequately aligned with the target distal point $P_d$ indicated by the laser $L_d$. On the other hand, as can be seen in FIG. 4A, the target point 209t on the guide 209g of the instrument 209 does not intersect with the laser $L_p$, which is directed toward the target proximal point $P_p$. This misalignment between the guide 209g and the laser $L_p$ causes the estimated trajectory $T_e$ of the instrument 209 (which assumes that the instrument 209 will be distally advanced and/or driven into the patient at the distal point $P_d$), when positioned as shown in FIG. 4A at time t0, to differ from the planned trajectory $T_o$. Moreover, the misalignment between the guide 209g and the laser $L_p$ indicates to the surgeon 205 or operator of the instrument 209 that the position of the tool, particularly the guide 209g and/or proximal end 209p must be adjusted to properly align the instrument 209 in accordance with the planned trajectory. As known to those of skill in the art, such adjustments can include rotating, pivoting or otherwise moving the instrument 209 to achieve a desired position and angle (e.g., relative to the patient).

FIG. 4B illustrates the instrument 209 at a second time period t1. In FIG. 4B, the instrument 209 has been adjusted by pivoting the guide 209g of the instrument 209, positioned at or proximate to the proximal end 209p. As illustrated, the guide 209g is pivoted away from the body of the patient 203 while the distal end 209d of the instrument 209 remains in contact or aligned with the target point Pd. As a result, the angle created between the instrument 209 and the patient 203 is altered such that the estimated trajectory $T_e$ based on the position of the instrument at time t1 is less shallow than the estimated trajectory at time t0.

As a result of the manipulation of the instrument 209 from time t0 to time t1, the target point 209t of the guide 209g is caused to be aligned with the laser $L_p$ directed at the point $P_p$. Alignment between the target point 209t and the laser $L_p$ means that the laser $L_p$ intersects with the point 209t. Moreover, the alignment of the target point 209t and the laser $L_p$ attained at time t1, together with the alignment of the distal end 209d of the instrument 209 with the distal target point $P_d$ results in the trajectory $T_e$ at time t1 overlapping with, being equal to, and/or having the same (or substantially the same) central longitudinal axis as the planned trajectory $T_o$ (as shown, for example, in FIGS. 4B and 4C). The surgeon 205 and/or other operator of the instrument 209 is thereby informed or prompted that the instrument 209 is properly aligned with the planned trajectory $T_o$, meaning that distal advancement of the instrument along its central longitudinal axis from its position at t0 will result in the instrument 209 moving through the patient's body in the planned path.

Returning to the trajectory guidance method illustrated in FIG. 3, steps 358 to 364 of FIG. 3 can be performed in real time, and can loop until the surgical procedure or step (e.g., implanting anchor) has been completed. That is, the laser system 207 can continuously and/or in real time: emit lasers (e.g., at step 358), monitor and/or track manipulations of the instrument 209 (e.g., at step 360), check whether the surgical procedure or step has been completed (e.g., at step 362), recalculate target points based on the manipulations of the instrument 209 (e.g., at step 364), and emit lasers based on the recalculated target points (e.g., at step 358), as explained in further detail below. The parameters that define the frequency and consistency of the loop can be based on factors such as hardware capabilities and type of surgery, for example, which can dictate the anticipated rate at which the position of the instrument is to be changed. FIG. 4C, described in further detail below, illustrates the result of adjusting the direction of the emitted lasers performed at steps 362, 364, and 358 based on the tracking of the manipulations of the instrument 209 performed at step 360.

That is, at step 360 of FIG. 3, the instrument 209 is operated by the surgeon 205 and/or other medical professional. As the tool is manipulated, the laser system 207 can obtain (e.g., via pushed or pulled data) tracking information about the instrument 209, including its actual and/or relative position, orientation, status (e.g., on, off state) and the like. The tracking information can be used to calculate changes of the tool relative to, for example, the laser system 207, other systems, devices or instruments, the patient 203, the planned trajectory $T_o$, and/or the lasers $L_p$ and/or $L_d$. The tracking information can be obtained by the laser system 207 continuously in real-time as the instrument is operated, based on a predetermined schedule (e.g., each second, twice per second, etc.), and/or when triggered by a condition (e.g., status of the instrument changes (e.g., on to off, off to on), force of the tool changes, etc.). The tracking information corresponding to the instrument 209 can be used for various purposes, including, as explained below, to measure the updated position of the instrument relative to the planned trajectory $T_o$ and/or adjust the direction in which the lasers $L_p$ and $L_d$ are emitted in order to continuously and accurately guide operation of the instrument 209.

It should be understood that although FIG. 3 references the tracking of changes related to the instrument 209, other information can be tracked during the operation in real time at step 360, including changes to systems, devices, instruments, and the patient. For example, if the patient is moved during surgery, those changes including the patient's orientation, position, and other relevant data can be obtained by the laser system 207.

The tracking of the instrument 209 performed at step 360 can be performed by the laser system 207, for example, using embedded or interconnected hardware and/or software such as cameras, sensors and the like, as described above in detail with reference to FIGS. 1-2B. In some embodiments, the tracking of the instrument 209 can be performed by or in conjunction with a surgical navigation system communicatively coupled to or integrated with the laser system 207. The navigation system can measure and/or track the instrument 209 during surgery and continuously or as needed transmit information to the laser system 207, such as a recalculation of laser target points $P_d$ and $P_p$. In turn, the laser system 207 can make adjustments or be driven to make adjustments to the laser outputs accordingly.

FIG. 4C illustrates the instrument 209 at a third time period t2, in which the instrument 209, at step 360, has been distally driven or advanced along the expected trajectory $T_e$ and/or planned trajectory $T_o$, which are equal or substantially equal to one another. As the instrument 209 is distally advanced at step 360, the laser system 207 (1) determines whether the surgical step or procedure with which the process 300 of FIG. 3 has been completed, and (2) if it has not been completed, the laser system 207 recalculates the laser target points $P_d$ and $P_p$ at step 364. The determination of whether the process is complete can be based on predetermined criteria or thresholds, such as time, trigger (e.g., on/off switch), position of the instrument 209, and others known to those of skill in the art.

If none of the process completion criteria are deemed to be met at step 362, the laser system 207 recalculates the target points $P_d$ and $P_p$ at step 364 in a process similar to that described above in connection with the laser target point calculation of step 356 but using updated information obtained during the tracking performed at step 360. For example, recalculating the target points can include determining an updated proximal point $P_p$ in the direction in which the laser $L_p$ is to be directed using the updated information relating to the instrument 209, such as its position and angle. In some embodiments, for instance, if the tool has been distally advanced a distance d from time t1

(FIG. 4B) to time t2 (FIG. 4C), the target point $P_p$ is moved a distance equal to distance d, or a distance that accounts for the distance d movement of the instrument 209. It should be understood that other identified or tracked changes can impact the recalculating of target points at step 364. For example, if the patient 203 is moved during surgery, the patient's new position can be accounted for in the recalculated target points $P_p$ and $P_d$. In turn, the process 300 returns to step 358, where the laser system 207 emits lasers or laser beams $L_p$ and $L_d$ based on the target points $P_d$ and $P_p$ recalculated at step 364.

In some embodiments, the real-time feedback loop of steps 358 to 364 illustrated in FIG. 3 enables the laser system 207 to recalculate the target points $P_p$ and $P_d$ as the instrument 209 is moved, causing the output lasers $L_p$ and $L_d$ to also move accordingly. The loop continues until the procedure or step is deemed to be completed at step 362, by identifying that a completion criteria has been met or triggered. In such a case, the process continues to step 366, where trajectory guidance is completed.

Figure 5A:
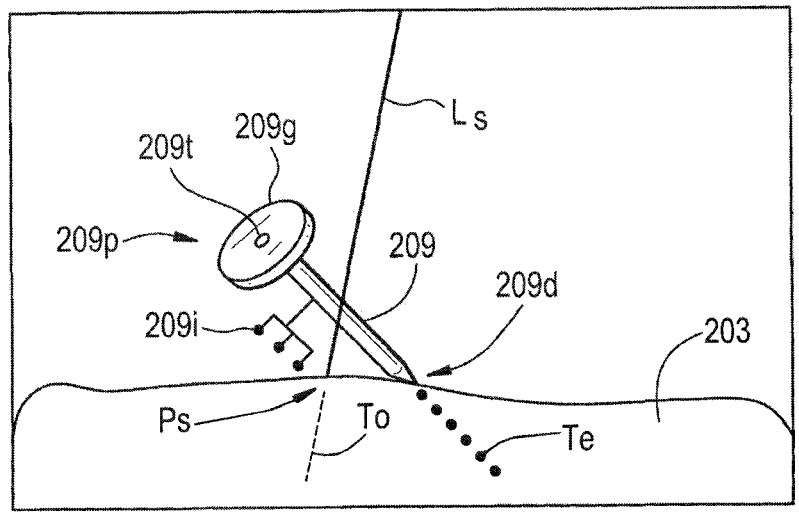
FIG. 5A is a diagram of one embodiment of a single emitted laser providing trajectory guidance for a surgical instrument at a first time period.
Figure 5B:
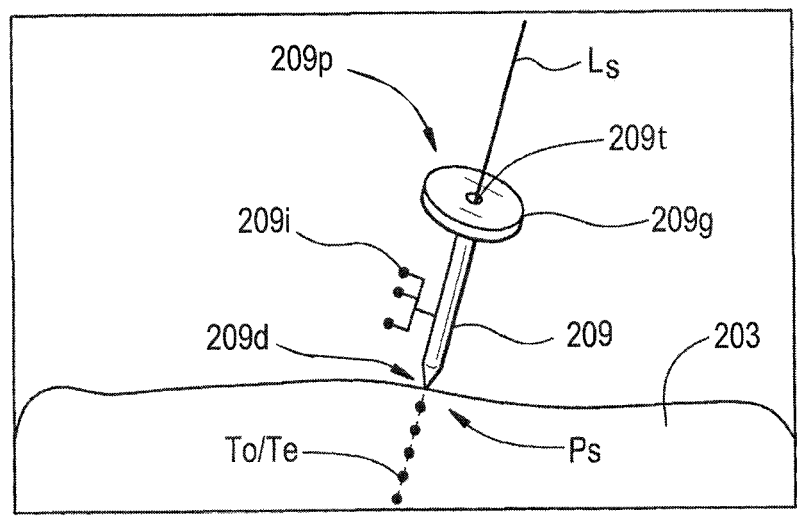
FIG. 5B is a diagram of one embodiment of a single emitted laser providing trajectory guidance for the surgical instrument of FIG. 5A at a second time period.

In some embodiments, laser-based trajectory guidance similar to the process illustrated in FIG. 3 can be performed using a single laser. That is, FIGS. 5A and 5B illustrate exemplary embodiments of the emission of the single laser $L_s$ toward a single target point Ps, to provide guidance for the planned trajectory $T_o$ of the instrument 209 into the patient 203. In the single laser trajectory guidance illustrated in FIGS. 5A and 5B, the single laser $L_s$ is used to indicate where the distal end 209d and the target point 209p on the guide 209g of the instrument 209 should be positioned to be accurately aligned with the planned trajectory $T_o$. That is, the distal target point where the laser $L_s$ is directed indicates where the distal end 209d should be aligned, while the rest of the laser $L_s$ indicates where at least the target point 209t should be aligned. It should be understood that the single target point $P_s$ is calculated such that the single laser $L_s$ is emitted along the same (or substantially the same) central longitudinal axis as that of the calculated planned trajectory $T_o$.

More specifically, FIG. 5A illustrates an exemplary embodiment of the emission of the single laser $L_s$ toward the single target point $P_s$ at a first time t0. The single laser $L_s$ is emitted not only to reach the calculated single target point $P_s$ on the body of the patient 203, but is also emitted from an output point that creates a laser path for the single laser $L_s$ that aligns with the planned trajectory $T_o$. As described above, the output point from which the laser can be emitted can be moved in the laser system and/or the laser system itself can be moved.

As shown in FIG. 5A, the instrument 209 is not aligned with the laser Ls, causing the instrument 209 to have an estimated trajectory $T_e$ different than the planned trajectory $T_o$. In order to properly align the instrument 209 in accordance with the planned trajectory $T_o$, both the proximal and distal end 209p and 209d of the instrument 209 must be adjusted by the surgeon 205 or other operator.

FIG. 5B illustrates an exemplary embodiment of the emission of the single laser $L_s$ toward the single target point $P_s$ at a second time t1. As shown, the single laser $L_s$ and target point $P_s$ remain constant, while the instrument 209 has been moved relative to its position at time t0. Specifically, the distal end 209d of the instrument 209 is moved and the proximal end 209p is pivoted, such that the distal end 209d aligns with the laser $L_s$ at the target point Ps, while the target point 209t on the guide 209g is aligned with a portion of the laser Ls. This alignment causes the planned trajectory $T_o$ and the estimated trajectory $T_e$ to overlap and/or be longitudinally aligned, meaning that they share a common or substantially common central longitudinal axis. The instrument 209, when properly aligned as shown in FIG. 5B, can in turn be distally advanced along the planned trajectory $T_o$. The single target point $P_s$ and the emitted laser $L_s$ can be adjusted in real-time, as needed, during the operation of the patient 203, to account for or remedy any changes (e.g., instrument position changes, patient movement, etc.)

Notably, the single and multi-laser trajectory guidance described above allows the surgeon 205 (and/or other operator of the instrument 209) to identify how the instrument 209 should be operated to conform with a calculated trajectory $T_o$ using visual aids (e.g., lasers) within the line of sight of the surgeon 205 and at or proximate to the surgical area (e.g., surgical entry point).

On-Instrument Trajectory Guidance

Figure 6:
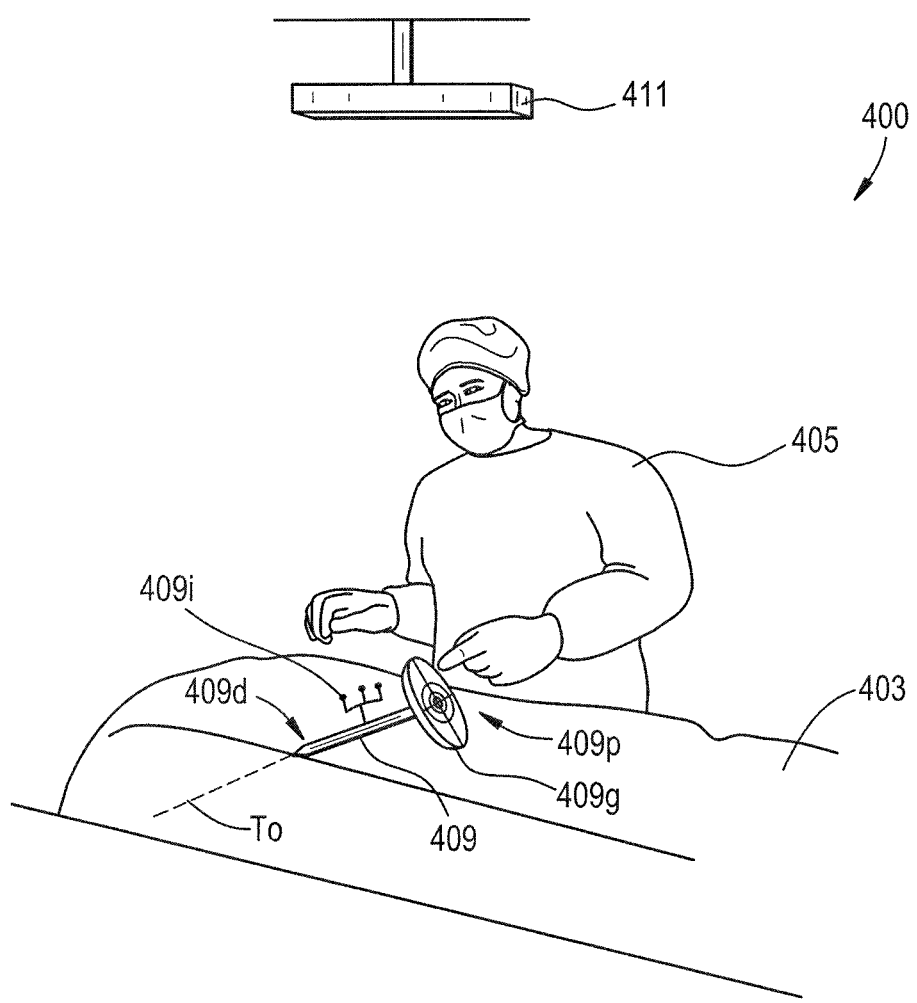
FIG. 6 is a diagram of one embodiment of a surgical environment including an on-instrument guide map for providing trajectory guidance.

FIG. 6 illustrates a surgical environment 400 including one exemplary embodiment of an instrument 409 configured to provide trajectory guidance. The instrument 409 can be or include guidewires, needles, taps, drivers, drills, cutters, blades, bone skids, retractors, access devices, and forceps, as well as implants such as bone anchors, spacers, cages, rods, plates, connectors, and the like. The instrument 409 includes a distal end 409d, initially positioned closest to the patient 403, and a proximal end 409p, initially positioned away from the patient 403. The instrument 409 can in some embodiments include a guide 409g configured to provide visual cues to the operator of the instrument 409 (e.g., surgeon 405), indicating how to align and operate the instrument 409 to replicate a calculated trajectory $T_o$, which is a path into and/or through the body of the patient 403. In some embodiments, the guide is fixed or removably attached at or proximate to the proximal end 409p of the instrument 409. As illustrated and described below in connection with FIGS. 7A to 7C, in some embodiments, the guide 409g can be or include a light-emitting diode (LED) map or the like, made up of segments that can be illuminated by LEDs to guide the alignment of the instrument 409. The LEDs can be illuminated in various ways known to those of skill in the art. It should be understood that the number and characteristics of the LEDs can vary as needed to conform with the objective of the LED map. Moreover, it should be understood that other types of light sources can be used to illuminate the map of the guide 409g.

The surgical environment 400 also includes a guidance system 411. The guidance system 411 can include hardware (e.g., memory, processors, communication means) and software configured to activate or trigger the guide 409g as needed to direct the instrument 409 to be aligned in accordance with the planned trajectory $T_o$ based, for example, on detection of a position of the instrument 409 using a navigation array 409i or other sensor or element coupled to the instrument (e.g., as described above with respect to surgical navigation systems employing optical sensors, electromagnetic sensors, inertial motion units, etc.). It should be understood that although the guidance system 411 is illustrated as an overhead system in the environment 400, the guidance system 411 can be made up of one or more communicatively coupled devices that can be provided at various locations within and outside of the surgical environment 400. In some embodiments, the guidance system 411 can calculate the planned trajectory $T_o$ as described herein based on information relating to the patient 403, the procedure and/or steps being performed on the patient, the instrument 409, and/or other communicatively coupled systems, devices and instruments. Such data can be captured by the system 411 and/or can be received from other systems.

It should be understood that, in some embodiments, the planned trajectory $T_o$ and/or information defining the planned trajectory $T_o$ can be calculated by a system other than the guidance system 411, and transmitted thereto. In some embodiments, the guidance system 411 includes navigation hardware and/or software, and/or is communicatively coupled to a navigation system. The navigation hardware and/or software can include cameras and/or other components configured to measure or detect information about the patient 403, instrument 409 and/or other systems and devices, such as position data. The information that is measured or detected by the navigation hardware and software of the guidance system 411 and/or the navigation system can be used, for example, to calculate the planned trajectory $T_o$ and/or track (e.g., in real-time) the instrument 409 during its operation. Based on the planned trajectory $T_o$ and the information relating to the instrument 409 (e.g., its actual or relative position), the guidance system 411 can transmit instructions to cause the guide 409g to be triggered to guide the position of the instrument 409 to be aligned with a planned trajectory.

Figure 7A:
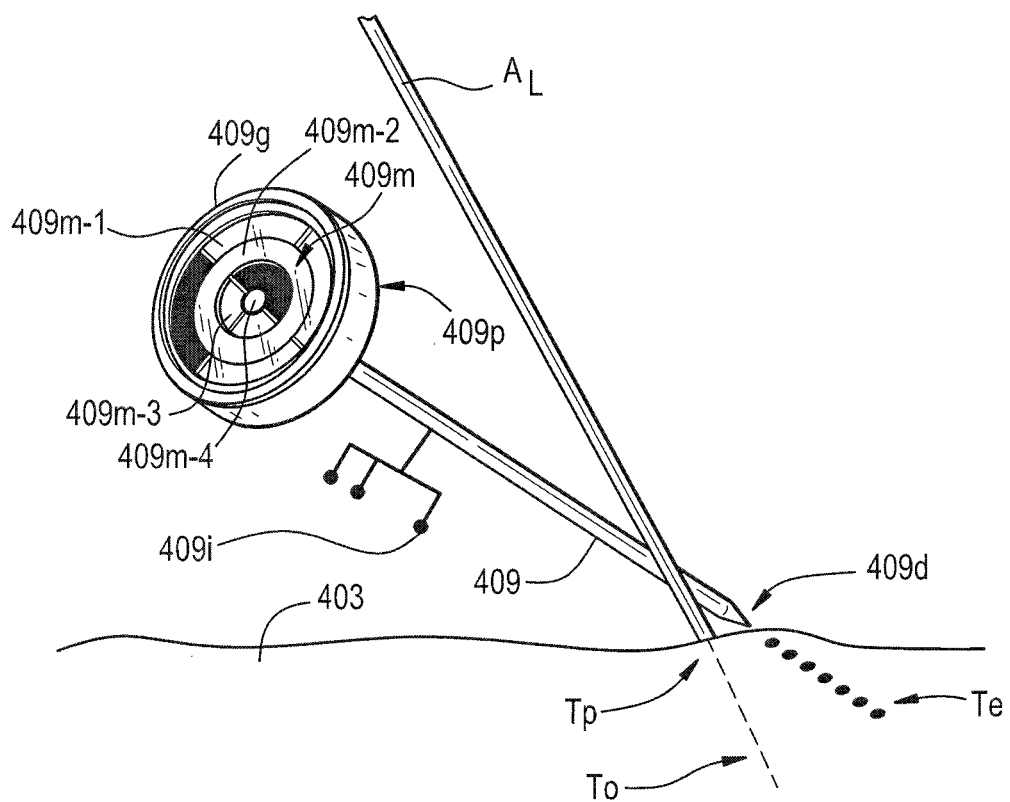
FIG. 7A is a diagram of one embodiment of an on-instrument guide map for providing trajectory guidance for a surgical instrument at a first time period.
Figure 7B:
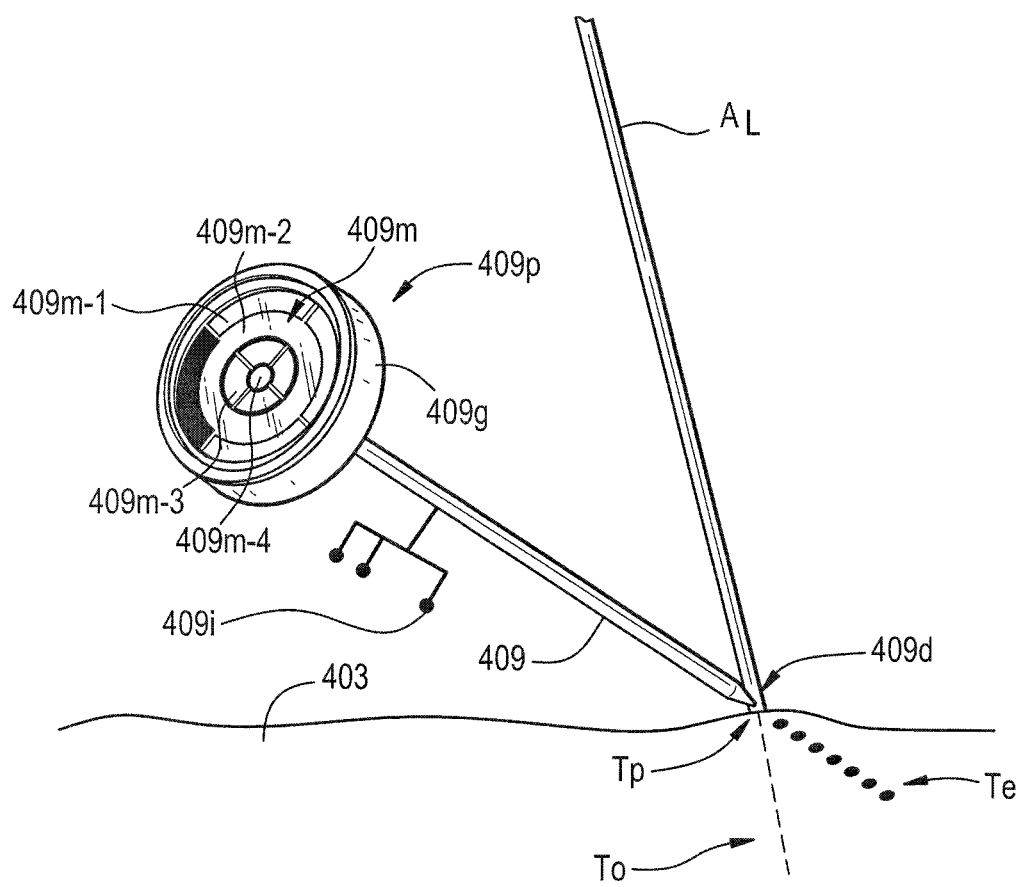
FIG. 7B is a diagram of one embodiment of the on-instrument guide map for providing trajectory guidance for the surgical instrument of FIG. 7B at a second time period.
Figure 7C:
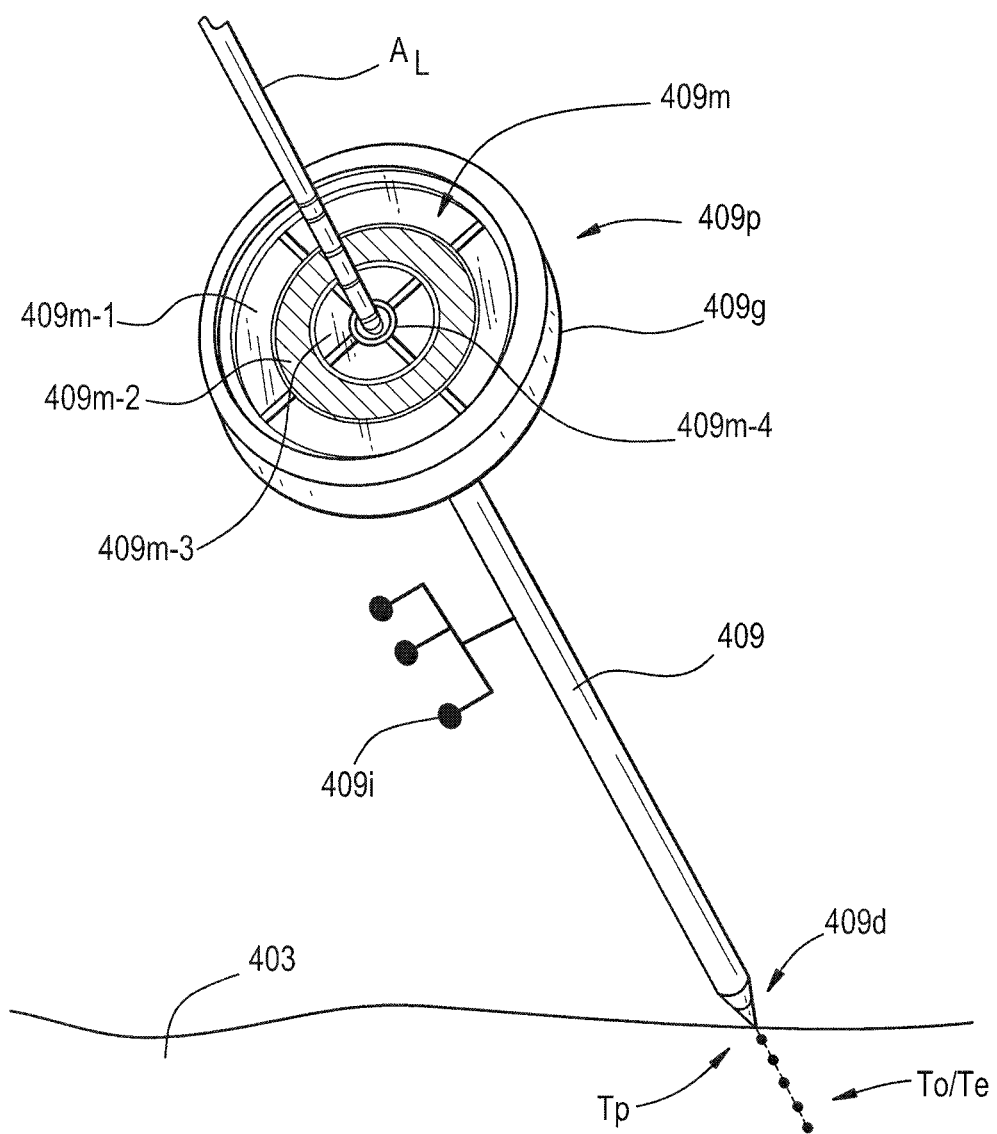
FIG. 7C is a diagram of one embodiment of the on-instrument guide map for providing trajectory guidance for the surgical instrument of FIGS. 7A and 7B at a third time period.

More specifically, FIGS. 7A, 7B, and 7C illustrate exemplary embodiments of the instrument 409 including guide 409g in the form of an LED map 409m to provide trajectory guidance during three sequential time periods t0 to t3, respectively. As shown, the map 409m includes four concentric circular areas 409m-1, 409m-2, 409m-3, and 409m-4 that include LEDs that can be activated to provide trajectory guidance by indicating how the distal end 409d and the proximal end 409p of the instrument should be moved to align the with the planned trajectory $T_o$, such that the central longitudinal axis of the instrument 409 is aligned with and/or matches the central longitudinal axis $A_L$ corresponding to the planned trajectory $T_o$. It should be understood that the central longitudinal axis $A_L$ corresponding to the planned trajectory $T_o$, while illustrated in FIGS. 7A-7C, is not visible (e.g., a visible laser) in the surgical environment and is merely intended to illustrate an alignment position for the instrument 409.

In the exemplary embodiments illustrated in FIGS. 7A-7C, the circular areas 409m-1 and 409m-2 correspond to the position of the proximal end 409p relative to the central longitudinal axis $A_L$ of the planned trajectory $T_o$, while the circular areas 409m-3 and 409m-4 correspond to the position of the distal end 40d relative to the central longitudinal axis $A_L$. Moreover, the circular areas 409m-2 and 409m-4, when illuminated, indicate alignment with the central longitudinal axis $A_L$, while the circular areas 409m-1 and 409m-3, when illuminated indicate misalignment with the central longitudinal axis $A_L$. The characteristics of the illuminated LEDs can vary based on the circular area. For example, circular areas 409m-2 and 409m-4, which indicate alignment, can be illuminated with a green color, while circular areas 409m-1 and 409m-3, which indicate misalignment, can be illuminated with a red color. Of course, other colors and characteristics can be used as well. Further, the circular areas 409m-1 and 409m-3, which indicate instrument misalignment, can be divided into sections (e.g., halves, quadrants) that, when illuminated, indicate the area or direction of the distal end or the proximal end of the instrument 409 having the largest distance from the central longitudinal axis $A_L$, which indicates the planned alignment position for the instrument 409.

As shown in FIG. 7A, the instrument 409 at time t0 is positioned such that its distal and proximal ends 409d and 409p, respectively, are misaligned with the central longitudinal axis $A_L$ corresponding of the planned trajectory $T_o$. This misalignment indicates that, if the instrument 409 is distally advanced along its central longitudinal axis when positioned as shown in FIG. 7A, its estimated trajectory $T_e$ into the body of the patient 403 would differ from the planned trajectory $T_o$. Accordingly, the instrument 409 causes LEDs to illuminate portions of the circular areas 409m-1 and 409m-3 to highlight the misalignment of the distal and proximal ends 409d and 409p with the central longitudinal axis $A_L$. Specifically, in some embodiments such as those illustrated in FIGS. 7A-7C, the circular areas 409m-1 and 409m-3 are divided into quadrants. When the distal and/or proximal ends of the instrument 409 are misaligned with the central longitudinal axis $A_L$, at least one quadrant of the circular areas 409m-1 and 409m-3 are illuminated, indicating that that quadrant is furthest positioned from the central longitudinal axis $A_L$. For example, in FIG. 7A, one quadrant is illuminated in the circular area 409m-1, indicating misalignment of the proximal end 409p in one of four directions, while two adjacent quadrants are illuminated in the circular area 409m-3, indicating misalignment of the distal end 409d in one of four directions. Thus, to properly align the instrument 409 with the central longitudinal axis $A_L$ of the planned trajectory $T_o$, the distal end 409d and/or the proximal end 409p of the instrument 409 must be adjusted such that the portion of the instrument 409 that is in the direction (or directions) of the illuminated quadrant (or quadrants) is (or are) moved toward the central longitudinal axis $A_L$.

FIG. 7B illustrates the instrument 409 at a time t1 after the time t0 corresponding to FIG. 7A. As shown in FIG. 7B, the instrument 409 has been adjusted relative to its position at time t0. That is, in FIG. 7B, at time t1, the distal end 409d has been moved in a direction opposite the illuminated quadrants of the circular area 409m-3. In other words, an area of the distal end 409d that corresponds to the illuminated quadrants of the circular area 409m-3 is drawn closer to the central longitudinal axis $A_L$. The distal end 409d is therefore placed in alignment with the central longitudinal axis $A_L$ at a target entry point $T_p$, meaning that the instrument 409 is partially aligned. The alignment of the distal end 409d can be indicated, as shown in FIG. 7B, by the LEDs in the circular area 409m-3 being turned off or darkened and/or by the circular area 409m-4 being illuminated. Still, the proximal end 409p remains misaligned as shown by the illuminated quadrant in the circular area 409m-1.

As described above, the LEDs of the LED map 409m can be illuminated by the instrument 409 and/or caused to be illuminated by the guidance system 411 as a result of its movement, which can be tracked in real-time or periodically (e.g., every 1 ms, 1 s, etc.) by the guidance system 411 (e.g., using its navigation hardware and/or software, or that of an independent navigation system). Thus, as the instrument 409 is moved and its adjusted position is identified by the guidance system 411, the guidance system 411 can determine which segments of the LED map 409m to illuminate based on the new relative position of the proximal or distal ends 409p and 409d, respectively, to the central longitudinal axis $A_L$. If the distal end 409d is moved between time t0 and t1 form a misaligned position to an aligned position as described above in connection with FIGS. 7A and 7B, the guidance system 411 can identify that the LEDs of the misalignment circular portion 409m-3 can be turned off and the alignment portion 409m-4 can be illuminated. Likewise, in some embodiments, if the distal end 409d is moved from one misaligned position to another, the guidance system 411 can identify the direction in which the distal end 409d needs to be moved in order to be aligned based on the newly tracked position, and illuminate portions of the circular are 409m-3 accordingly.

FIG. 7C illustrates the instrument 409 at a time t2 after the time t1 corresponding to FIG. 7B. As shown in FIG. 7C, the instrument 409 at time t2 has been adjusted relative to its position at time t1. That is, in FIG. 7C, at time t2, the proximal end 409p has been moved in a direction opposite the illuminated quadrant of the circular area 409m-1. In other words, an area of the proximal end 409p that corresponds to the illuminated quadrant of the circular area 409m-1 is drawn closer to the central longitudinal axis $A_L$. The proximal end 409p is therefore placed in alignment with the central longitudinal axis $A_L$ at an area other than at the target entry point $T_p$, meaning that the instrument 409m is fully aligned (assuming the distal end remains in alignment, as in FIG. 7C). The alignment of the proximal end 409p can be indicated, as shown in FIG. 7C, by the LEDs in the circular area 409m-1 being turned off or darkened and/or by the circular area 409m-2 being illuminated.

Similar to the illumination of the LEDs of the LED map 409m described above in connection with FIG. 7B, the activated LEDs illustrated in FIG. 7C can be illuminated by the instrument 409 and/or caused to be illuminated by the guidance system 411 as a result its tracked movements. Thus, although not illustrated, as the proximal end 409p of the instrument is manipulated between times t1 (FIG. 7B) and t2 (FIG. 7C), the guidance system 411 identifies the movements, determines the position of the proximal end 409p relative to the central longitudinal axis $A_L$ of the planned trajectory $T_o$, and illuminates or turns off respective LEDs based on the alignment or misalignment of the proximal end central longitudinal axis $A_L$ of the planned trajectory $T_o$.

As shown in FIG. 7C, the instrument 409 is fully aligned with the central longitudinal axis $A_L$ at both its proximal and distal ends 409p and 409d, respectively. The full alignment of the proximal and distal ends 409p and 409d is indicated by (1) the illumination of alignment circular areas 409m-2 and 409m-4, respectively, and (2) the non-illumination of misalignment circular areas 409m-1 and 409m-2, respectively. Alignment of the proximal and distal ends 409p and 409d with the central longitudinal axis $A_L$ means that, if the instrument 409 is distally advanced (e.g., along its central longitudinal axis) into the patient 403, its estimated trajectory $T_e$ will match substantially match the planned trajectory $T_o$.

It should be understood that the map 409m can have shapes other than those illustrated in FIGS. 6 and 7A-7C (e.g., hexagon, triangle, square) and different dimensions (e.g., diameter). Moreover, the map can be illuminated using a variety of illumination sources other than LEDs, as known to those. The map 409m can be illuminated in a number of different ways. For example, entire segments can be illuminated, or portions of a segment can be illuminated. In some embodiments, a circular area can be made up of adjacent light sources, each of which can be individually illuminated to show alignment or misalignment. It should be understood that the number of circular (or otherwise shaped areas) on the map 409m can vary and can have different purposes. For example, while the outermost circular area 409m-1 in FIGS. 7A-7C corresponds to the alignment of the proximal end of the instrument 409, that same area could instead be used to show misalignment of the distal end of the instrument 409. In some embodiments, the guide 409g and/or map 409m can be made up of a single circular area made up of adjacent LEDs or the like, each of the LEDs being configured to be illuminated to show alignment or misalignment. For instance, portions of the circular area can be illuminated or illuminated using a particular color (e.g., green) to show a corresponding alignment, while other portions of the circular area can be darkened, not illuminated or illuminated using a different color (e.g., green) to show misalignment. As known to those of skill in the art, the guide 409g and/or map 409m can be configured in various ways to indicate alignment of proximal and distal ends of the instrument 409.

The guide 409g of the instrument 409 described above provides trajectory guidance to the operator of the instrument using visual cues, by indicating whether the proximal and distal ends of the instrument are properly aligned to replicate and/or adhere to a planned trajectory $T_o$. It should be understood that the guide 409g can be used not only to indicate whether the instrument 409 is aligned with the planned trajectory $T_o$, but also to indicate or alert when the instrument (e.g., the distal end of the instrument) is approaching or within a predetermined distance of a planned or non-planned structure. For example, visual cues such as those described above can indicate when the instrument is proximate to or has reached a desired structure (e.g., a bone or bone depth to be operated on) by illuminating a respective area on the map 409m using green lights, or by illuminating a respective area on the map 409m when the instrument is proximate to or has reached a non-planned structure (e.g., nerve). Such guidance can be provided based on information obtained by the guidance system, including, for example, pre-operative patient data (e.g., patient images). Such guidance can also be provided based on information obtained using other sensors disposed in an operating theater and/or coupled to the instrument 409. For example, information regarding proximity to nerves or other neural tissues or structures can be provided using one or more sensors integrated into the instrument 409. Such sensors can include one or more electrodes to detect the presence of, and proximity to, nerves. Exemplary sensors include those used in connection with electromyography (EMG) and mechanomyography (MMG).

Moreover, while the guide 409g of the instrument 409 described above provides trajectory guidance to the operator of the instrument using visual cues, the instrument 409 can be configured to, additionally or alternatively, provide non-visual cues to the operator of the instrument 409, such as haptic and/or audio cues, prompts or feedbacks. For example, the instrument 409 (e.g., at a handle or shaft portion) can be configured to vibrate (or vibrate in various ways) to provide guidance to the instrument operator. For example, vibration and other haptic cues can be used to indicate when the instrument is aligned or misaligned with the axis of the planned trajectory, or when the instrument is proximate or adjacent to a desired or planned structure. Moreover, such guidance can be provided through audio cues, ranging from indirect feedback (e.g., rings, dings, beeps, and the like) to more direct feedback (e.g., spoken cues such as "distal end left," "proximal end right," "danger").

Figure 8:
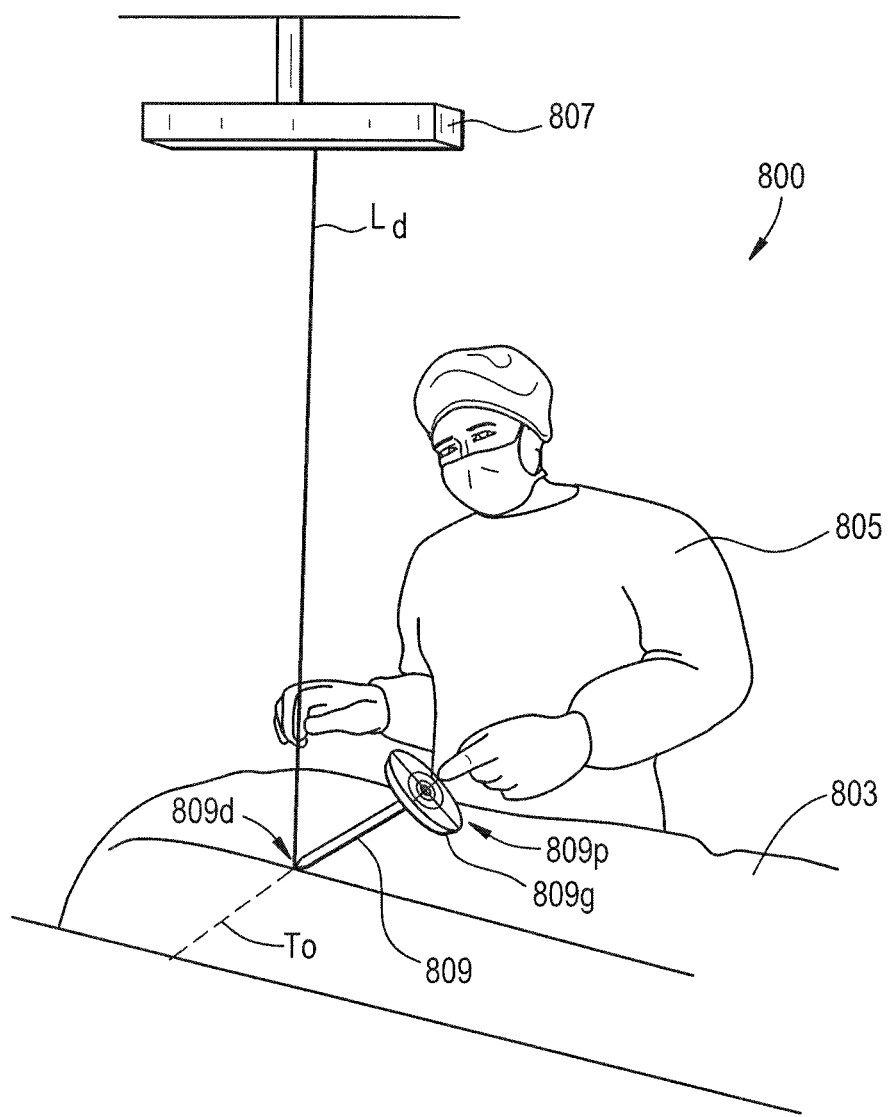
FIG. 8 is a diagram of another embodiment of a surgical environment including an on-instrument guide map for providing trajectory guidance.

FIG. 8 illustrates another surgical environment 800 including one embodiment of an instrument 809 configured to provide trajectory guidance. The instrument 809 can be or include guidewires, needles, taps, drivers, drills, cutters, blades, bone skids, retractors, access devices, and forceps, as well as implants such as bone anchors, spacers, cages, rods, plates, connectors, and the like. The instrument 809 includes a distal end 809d, initially positioned closest to the patient 803, and a proximal end 809p, initially positioned away from the patient 803. Similar to the instrument 409 described above, the instrument 809 can include a guide 809g configured to provide visual cues to the operator of the instrument 809 (e.g., surgeon 805), indicating how to align and operate the instrument 809 to replicate a calculated trajectory $T_o$, which is a path into and/or through the body of the patient 803. In some embodiments, the guide is fixed or removably attached at or proximate to the proximal end 809p of the instrument 809. As described above, the guide 409g can be or include a light-emitting diode (LED) map or the like, made up of segments that can be illuminated by LEDs to guide the alignment of the instrument 409.

In the embodiment shown in FIG. 8, the guide 409g can also include an inertial motion sensor, such as a gyroscopic sensor, to detect its orientation in at least two planes. The instrument 409 with guide 409g can be used in combination with a single laser system 807 to provide trajectory guidance to a user according to a planned trajectory. For example, the laser system 807 can be configured to project a single laser $L_d$ onto the patient 803 at a location where the distal end of the instrument 409 is to be inserted. With the distal end 809d of the instrument positioned at the location of the laser projection, the inertial sensor of the guide 409g can be utilized to direct a user's pivoting motion of the instrument about the position of the distal end 809d to align the instrument 409 with the planned or desired trajectory $T_o$. By way of further example, the LED map or other indicators on the guide 409g can indicate to a user whether to, e.g., pivot left/right and/or up/down about the distal end 809d of the instrument to achieve the desired alignment. Note that in such an embodiment, the instrument 409 need not be tracked using a surgical navigation system, as the position of the distal end 809d can be assumed to match the position of the laser $L_d$ and the inertial motion sensor of the guide 409g can be used to determine movements necessary for the proximal end 809p. In order to facilitate this, the guide 409g can be in communication (e.g., wireless communication) with the laser system 807 to receive desired alignment information, or such information can be downloaded to the guide 409g prior to use. Moreover, in some embodiments a surgical navigation system can be utilized with the instrument 409, either in addition to or instead of the inertial motion sensor in the guide 409g.

The example embodiments described above, including the systems and procedures depicted in or discussed in connection with FIGS. 1-8, or any part or function thereof, may be implemented by using hardware, software, or a combination of the two. The implementation may be in one or more computers or other processing systems. Portions of the example embodiments described herein may be conveniently implemented by using a conventional general purpose computer, a specialized digital computer and/or a microprocessor programmed according to the teachings of the present disclosure, as is apparent to those skilled in the computer art. Appropriate software coding may readily be prepared by skilled programmers based on the teachings of the present disclosure. Some embodiments may also be implemented by the preparation of application-specific integrated circuits, field programmable gate arrays, or by interconnecting an appropriate network of conventional component circuits. Some embodiments can include a computer program product. The computer program product may be a non-transitory storage medium or media having instructions stored thereon or therein which can be used to control, or cause, a computer to perform any of the procedures of the example embodiments described herein.

In addition, it should be understood that the figures are presented for example purposes only. The architecture of the example embodiments presented herein is sufficiently flexible and configurable, such that it may be utilized and navigated in ways other than that shown in the accompanying figures. It is also to be understood that the procedures recited in the claims need not be performed in the order presented. Although specific embodiments are described above, it should be understood that numerous changes may be made within the spirit and scope of the concepts described. Accordingly, the disclosure is not to be limited by what has been particularly shown and described. All publications and references cited herein are expressly incorporated herein by reference in their entirety.

The invention claimed is:

1. A system for providing trajectory guidance, comprising:
one or more laser output devices operable to emit lasers and independently control pointing of the lasers along two or more beam trajectories, and
at least one processor communicatively coupled to the one or more laser output devices, the at least one processor being operable to:
calculate a planned trajectory within an object based on first object data corresponding to the object, the planned trajectory indicating a target path for distally and proximally moving one or more instruments in a id out of the object;
obtain actual data including at least second object data corresponding to the object and first instrument data corresponding to an instrument from among the one or more instruments;
perform calibration on the object and the instrument based on the actual data and the planned trajectory;
calculate two or more target points based on the actual data and the planned trajectory, each of the two or more target points indicating a position toward which to direct one or more lasers respectively emitted from the one or more laser output devices; and
cause to point and emit the one or more lasers toward the two or more target points,
wherein the two or more target points are calculated such that the emitted one or more lasers guide the instrument to a planned alignment corresponding to the planned trajectory,
wherein the two or more target points include a proximal target point and a distal target point indicating a position towards which to direct a proximal laser and a distal laser, respectively,
wherein the planned alignment is a position in which: (1) a distal end of the instrument intersects with the distal laser, and (2) the proximal end of the instrument intersects with the proximal laser, and
wherein a first path of the proximal laser to the proximal target point is different from a second path of the distal laser to the distal target point, the first and second paths being set independently by the one or more laser output devices.

2. The system of claim 1, wherein the planned alignment of the instrument is a position in which a central longitudinal axis of the instrument is the same as a central longitudinal axis of the planned trajectory.

3. The system of claim 1,
wherein the proximal end includes a guide having a target point thereon, and
wherein the proximal end of the instrument intersects with the proximal laser at the target point of the guide when the instrument is in the planned alignment.

4. The system of claim 3, wherein the distal end of the instrument intersects with the distal laser at an entry point into the object, the entry point corresponding to a proximal end of the planned trajectory.

5. The system of claim 4, wherein in the planned alignment, if the instrument is distally advanced, the instrument moves along the planned trajectory.

6. The system of claim 1, wherein the processor is further operable to:
obtain updated actual data including at least updated first instrument data;
recalculate the two or more target points based on the updated actual data and the planned trajectory,
wherein the one or more lasers are caused to be emitted toward the one or more updated laser target points.

7. The system of claim 6, wherein the updated actual data is based on operating of the instrument.

8. The system of claim 7, wherein the obtaining of the updated actual data, recalculating the two or more target points, and causing the one or more lasers to be emitted is performed in real-time during the operating of the instrument.

9. A method for providing trajectory guidance, comprising:
calculating a planned trajectory within an object based on first object data corresponding to the object, the planned trajectory indicating a target path for distally and proximally moving one or more instruments in and out of the object;
obtaining actual data including at least second object data corresponding to the object and first instrument data corresponding to an instrument from among the one or more instruments;
performing calibration on the object and the instrument based on the actual data and the planned trajectory;
calculating two more target points based on the actual data and the planned trajectory, each of the two or more target points indicating a position toward which to direct one or more lasers respectively emitted from the one or more laser output devices;
independently pointing the one or more laser output devices toward each of the two or more target points; and
emitting, from the one or more laser output devices, the one or more lasers toward the two or more target points,
wherein the two or more target points are calculated such that the emitted one or more lasers guide the instrument to a planned alignment corresponding to the planned trajectory,
wherein the two or more target points include a proximal target point and a distal target point indicating a position towards which to direct a proximal laser and a distal laser, respectively,
wherein the planned alignment is a position in which: 1) a distal end of the instrument intersects with the distal laser, and (2) the proximal end of the instrument intersects with the proximal laser, and
wherein a first path of the proximal laser to the proximal target point is different from a second path of the distal laser to the distal target point, the first and second paths being set independently by the one or more laser output devices.

10. The method of claim 9, wherein the planned alignment of the instrument is a position in which a central longitudinal axis of the instrument is the same as a central longitudinal axis of the planned trajectory.

11. The method of claim 9,
wherein the proximal end includes a guide having a target point thereon, and
wherein the proximal end of the instrument intersects with the proximal laser at the target point of the guide when the instrument is in the planned alignment.

12. The method of claim 11, wherein the distal end of the instrument intersects with the distal laser at an entry point into the object, the entry point corresponding to a proximal end of the planned trajectory.

13. The method of claim 12, wherein in the planned alignment, if the instrument is distally advanced, the instrument moves along the planned trajectory.

14. The method of claim 9, further comprising:
obtaining updated actual data including at least updated first instrument data;
recalculating the two or more target points based on the updated actual data and the planned trajectory,
wherein the one or more lasers are caused to be emitted toward the one or more updated laser target points.

15. The method of claim 14, wherein the updated actual data is based on operating of the instrument.

16. The method of claim 15, wherein the obtaining of the updated actual data, recalculating the two or more target points, and causing the one or more lasers to be emitted is performed in real-time during the operating of the instrument.

\* \* \* \* \*